US012042533B2

(12) United States Patent
Tobin et al.

(10) Patent No.: US 12,042,533 B2
(45) Date of Patent: Jul. 23, 2024

(54) IRRADIATION-INACTIVATED POLIOVIRUS, COMPOSITIONS INCLUDING THE SAME, AND METHODS OF PREPARATION

(71) Applicants: BIOLOGICAL MIMETICS, INC., Frederick, MD (US); THE HENRY M. JACKSON FOUNDATION FOR THE ADVANCEMENT OF MILITARY MEDICINE, INC., Bethesda, MD (US)

(72) Inventors: Gregory J. Tobin, Frederick, MD (US); Michael J. Daly, Washington, DC (US)

(73) Assignees: BIOLOGICAL MIMETICS, INC., Frederick, MD (US); THE HENRY M. JACKSON FOUNDATION FOR THE ADVANCEMENT OF MILITARY MEDICINE, INC, Bethesda, MD (US)

( * ) Notice: Subject to any disclaimer, the term of this patent is extended or adjusted under 35 U.S.C. 154(b) by 732 days.

(21) Appl. No.: 17/041,870

(22) PCT Filed: Mar. 29, 2019

(86) PCT No.: PCT/US2019/024836
§ 371 (c)(1),
(2) Date: Sep. 25, 2020

(87) PCT Pub. No.: WO2019/191586
PCT Pub. Date: Oct. 3, 2019

(65) Prior Publication Data
US 2021/0128713 A1 May 6, 2021

Related U.S. Application Data

(60) Provisional application No. 62/650,406, filed on Mar. 30, 2018.

(51) Int. Cl.
*A61K 39/12* (2006.01)
*C12N 7/04* (2006.01)
(Continued)

(52) U.S. Cl.
CPC ............... *A61K 39/12* (2013.01); *C12N 7/04* (2013.01); *C12N 13/00* (2013.01);
(Continued)

(58) Field of Classification Search
None
See application file for complete search history.

(56) References Cited

U.S. PATENT DOCUMENTS 9,186,406 B2   11/2015   Daly et al.
9,234,168 B2   1/2016   Daly et al.
(Continued)

FOREIGN PATENT DOCUMENTS

JP   2008088066 A   4/2008
JP   2013525456 A   6/2013
(Continued)

OTHER PUBLICATIONS

Gayen et al. (Vaccine. 2017; 35: 3672-3681).*
(Continued)

*Primary Examiner* — Shanon A. Foley
(74) *Attorney, Agent, or Firm* — Myers Bigel, P.A.

(57) ABSTRACT

Compositions useful as poliovirus immunogens are provided along with methods and compositions for preparing the same. Compositions comprising poliovirus immunogens can enable a host response that includes virus-neutralizing antibodies which can protect the host from infection and/or disease.

17 Claims, 9 Drawing Sheets

Specification includes a Sequence Listing.

(51) Int. Cl.
  *C12N 13/00* (2006.01)
  *A61K 39/00* (2006.01)
(52) U.S. Cl.
  CPC .............. *A61K 2039/5252* (2013.01); *C12N 2770/32634* (2013.01); *C12N 2770/32661* (2013.01)

(56) References Cited

U.S. PATENT DOCUMENTS

| | | | |
|---|---|---|---|
| 9,758,760 B2 | 9/2017 | Daly et al. | |
| 2006/0257877 A1* | 11/2006 | Anderle | A61P 31/12 435/6.18 |
| 2010/0158945 A1* | 6/2010 | MacAdam | A61P 31/12 424/217.1 |
| 2013/0209508 A1* | 8/2013 | Daly | A61K 39/0258 424/234.1 |
| 2017/0087240 A1 | 3/2017 | Sanders et al. | |
| 2021/0128713 A1* | 5/2021 | Tobin | C12N 7/04 |

FOREIGN PATENT DOCUMENTS

| | | |
|---|---|---|
| KR | 20040050346 A | 6/2004 |
| WO | 2009045655 A2 | 4/2009 |
| WO | 2011139881 A2 | 11/2011 |
| WO | 2013095781 A1 | 6/2013 |
| WO | 2014155297 A2 | 10/2014 |

OTHER PUBLICATIONS

Gaidamakova et al. (Cell Host and Microbe. 2012: 12: 117-24).*
Berlett et al. (Redox Report. 2014; 19 (2): 80-86).*
Muller et al. (Scientific Reports. 2016; 6 (1): 22094).*
Berlett et al. "Designing antioxidant peptides" Redox Report, 19(2):80-86 (2014).
Extended European Search Report corresponding to European Patent Application No. 19776816.1 (13 pages) (dated Jan. 12, 2022).
Fogh, Jorgen "Ultraviolet Light Inactivation of Poliomyelitis Virus" Experimental Biology and Medicine, 89(3):464-465 (1955).
Helentjaris et al. "Inhibition of Host Cell Protein Synthesis by UV-Inactivated Poliovirus" Journal of Virology, 21(1):259-267 (1977).
Simizu et al. "Development of inactivated poliovirus vaccine derived from Sabin strains" Biologicals, 34:151-154 (2006).
Tano et al. "Antigenic characterization of a formalin-inactivated poliovirus vaccine derived from live-attenuated Sabin strains" Vaccine, 25:7041-7046 (2007).
International Search Report and Written Opinion corresponding to PCT/US2019/024836 dated Sep. 19, 2019, 13 pages.
Gayen, et al., "Deinococcus Mn2+-peptide complex: A novel approach to alphavirus vaccine development" Vaccine, 35(29):3672-3681 2017.
Wilton, Thomas, "Molecular characterisation of poliovirus inactivation with formaldehyde or other alternative chemical compounds" Imperial College London, Department of Medicine, Thesis for Doctor of Philosophy 2012, 292 pages.
Dabral et al. "Oral Immunization of Mice with Gamma-Irradiated Brucella neotomae Induces Protection against Intraperitoneal and Intranasal Challenge with Virulent B. abortus 2308" PLoS ONE, 9(9):e107180 (2014).
Daly et al. "Accumulation of Mn(II) in Deinococcus radiodurans Facilitates Gamma-Radiation Resistance" Science, 306(5698):1025-1028 (2004).
Daly et al. "Small-Molecule Antioxidant Proteome-Shields in Deinococcus radiodurans" PLoS One, 5(9):e12570 (2010).
Gaidamakova et al. "Preserving Immunogenicity of Lethally Irradiated Viral and Bacterial Vaccine Epitopes Using a Radio-Protective Mn2+-Peptide Complex from Deinococcus" Cell Host & Microbe, 12:117-124 (2012).
Honnold et al. "Second Generation Inactivated Eastern Equine Encephalitis Virus Vaccine Candidates Protect Mice against a Lethal Aerosol Challenge" PLoS ONE, 9(8):e104708 (2014).

* cited by examiner

FIG. 5

| Serum Sample | Dose MDP | Neutr titer | Linear mean | Log-2 titer | Log-2 mean |
|---|---|---|---|---|---|
| C30-1 | 1X + MDP | 2330 | 1960.0 | 11.2 | 9.7 |
| C30-2 | | 113 | | 6.8 | |
| C30-3 | | 980 | | 9.9 | |
| C30-4 | | 1960 | | 10.9 | |

| Serum Sample | Dose MDP | Neutr titer | Linear mean | Log-2 titer | Log-2 mean |
|---|---|---|---|---|---|
| C31-1* | 1X - MDP | 1 | 229.3 | 0.0 | 4.4 |
| C31-2 | | 536 | | 9.1 | |
| C31-3 | | 379 | | 8.6 | |
| C31-4* | | 1 | | 0.0 | |

| Serum Sample | Dose MDP | Neutr titer | Linear mean | Log-2 titer | Log-2 mean | Serum Sample | Dose MDP | Neutr titer | Linear mean | Log-2 titer | Log-2 mean |
|---|---|---|---|---|---|---|---|---|---|---|---|
| C22-1 | 2X + MDP | 5170 | 11345.0 | 12.3 | 12.8 | C26-1 | 2X + MDP | 17300 | 8555.5 | 14.1 | 12.3 |
| C22-2 | | 9470 | | 13.2 | | C26-2 | | 2540 | | 11.3 | |
| C22-3 | | 1640 | | 10.7 | | C26-3 | | 13400 | | 13.7 | |
| C22-4 | | 29100 | | 14.8 | | C26-4 | | 982 | | 9.9 | |
| C23-1 | 1X + MDP | 13400 | 15534.5 | 13.7 | 13.2 | C27-1 | 1X + MDP | 982 | 1724.4 | 9.9 | 9.8 |
| C23-2 | | 15900 | | 14.0 | | C27-2 | | 1170 | | 10.2 | |
| C23-3 | | 18900 | | 14.2 | | C27-3 | | 450 | | 8.8 | |
| C23-4 | | 536 | | 9.1 | | C27-4 | | 226 | | 7.8 | |
| C23-5 | | 2540 | | 11.3 | | C27-5 | | 757 | | 9.6 | |
| C23-6 | | 17300 | | 14.1 | | C27-6 | | 450 | | 8.8 | |
| C23-7 | | 14600 | | 13.8 | | C27-7 | | 1070 | | 10.1 | |
| C23-8 | | 41100 | | 15.3 | | C27-8 | | 8690 | | 13.1 | |
| C24-1 | 1/2X + MDP | 9470 | 6449.6 | 13.2 | 12.1 | C28-1 | 1/2X + MDP | 4350 | 6122.6 | 12.1 | 10.9 |
| C24-2 | | 2330 | | 11.2 | | C28-2 | | 899 | | 9.8 | |
| C24-3 | | 5180 | | 12.3 | | C28-3 | | 56.6 | | 5.8 | |
| C24-4 | | 347 | | 8.4 | | C28-4 | | 10300 | | 13.3 | |
| C24-5 | | 14600 | | 13.8 | | C28-5 | | 95.1 | | 6.6 | |
| C24-6 | | 6700 | | 12.7 | | C28-6 | | 8690 | | 13.1 | |
| C24-7 | | 5650 | | 12.5 | | C28-7 | | 20600 | | 14.3 | |
| C24-8 | | 7320 | | 12.8 | | C28-8 | | 3990 | | 12.0 | |
| C25-1 | 1/8X + MDP | 147 | 3921.8 | 7.2 | 11.0 | C29-1 | 1/8X + MDP | 30.8 | 32.8 | 4.9 | 5.0 |
| C25-2 | | 7300 | | 12.8 | | C29-2 | | 28.3 | | 4.8 | |
| C25-3 | | 5650 | | 12.5 | | C29-3 | | 28.3 | | 4.8 | |
| C25-4 | | 2590 | | 11.3 | | C29-4 | | 43.6 | | 5.4 | |

FIG. 9

UVC-inactivated PV3 Sabin

IRRADIATION-INACTIVATED POLIOVIRUS, COMPOSITIONS INCLUDING THE SAME, AND METHODS OF PREPARATION

STATEMENT OF PRIORITY

This application is a 35 U.S.C. § 371 national stage application of PCT International Application No. PCT/US2019/024836, filed Mar. 29, 2019, which claims the benefit, under 35 U.S.C. § 119(e), of U.S. Provisional Application No. 62/650,406, filed on Mar. 30, 2018, the entire contents of each of which are incorporated by reference herein.

STATEMENT OF GOVERNMENT SUPPORT

This invention was made with government support under 2R44AI120260-02 and 1R43AI120260-01 awarded by the National Institutes of Health, and HDTRA 1-17-C-0030 and HDTRA1-15-P-0034 awarded by the Department of Defense. The government has certain rights in this invention.

STATEMENT REGARDING ELECTRONIC FILING OF A SEQUENCE LISTING

A Sequence Listing in ASCII text format, submitted under 37 C.F.R. § 1.821, entitled 1472-2 ST25.txt, 937 bytes in size, generated on Sep. 24, 2020 and filed via EFS-Web, is provided in lieu of a paper copy. This Sequence Listing is hereby incorporated herein by reference into the specification for its disclosures.

FIELD

The present invention relates to compositions including irradiation-inactivated poliovirus immunogens and to methods and compositions for preparing the same.

BACKGROUND

The chemically-inactivated and live attenuated poliovaccines have been effective in stimulating protective immunity and eradicating poliomyelitis from the majority of countries across the world. The first polio vaccine, inactivated polio vaccine (IPV), was developed by Dr. Jonas Salk, is composed of formalin-inactivated poliovirus Types 1, 2, and 3, and was first used in 1955. The second polio vaccine, oral poliovaccine (OPV), was developed by Dr. Albert Sabin and is composed of live poliovirus Types 1, 2, and 3 that have been attenuated for pathogenesis. Due to its low cost compared to IPV, the OPV became the dominant vaccine and has been used extensively in vaccination campaigns in an effort to achieve global eradication.

Both the OPV and IPV have flaws that will eventually render them obsolete. After inoculation with OPV, the virus replicates in the intestine and stimulates robust immunity. However, during this replication process, the three virus components can lose their attenuated phenotype and neuropathogenic progeny virus can be excreted. With the reduction of polio infections caused by natural wild-type strains, the relative incidence of infection and disease caused by vaccine-derived poliovirus (VDPV) has become more significant. Now that wild-type poliovirus Type 2 has been eradicated, the World Health Organization (WHO) has recommended the use of a bivalent OPV consisting of attenuated Types 1 and 3. Although the number of infections caused by VDPV is relatively small, the numbers will be intolerable upon completion of global eradication. For this reason, the majority of countries have transitioned to using the IPV instead of OPV.

IPV is manufactured from large-scale production of wild-type, neuropathogenic strains of PV1, PV2, and PV3. The purified virus is concentrated and inactivated by incubation for 2-4 weeks with formalin. IPV stimulates robust systemic immunity. After global eradication, the WHO and other world health authorities plan for continued vaccination for 10 years or more to ensure that the immune protection in the general population remains strong enough to counteract potential exposures from residual poliovirus in the environment. Once this approximate 10 year post-eradication vaccination period is concluded, it is likely that many countries will phase out polio vaccinations. With waning global immunity after eradication, the continued use of large quantities of neuropathogenic strains creates an increasingly serious biohazard.

Efforts to replace the neuropathogenic strains in IPV with attenuated (Sabin) strains have resulted in mixed results. Most notably, formalin treatment inactivates a major neutralization epitope in the VP1 capsid protein of the Type 1 Sabin virus. Although some countries have licensed IPV vaccines composed of formalin-inactivated Sabin strains, the effectiveness of the Type 1 component is unknown.

Vaccination is to be the most effective countermeasure to prevent poliovirus infections and disease.

SUMMARY

The invention relates, in part, to poliovirus antigens based on attenuated and/or neuropathogenic strains of poliovirus that are inactivated by exposure to ionizing radiation (e.g., gamma and/or x-ray radiation) and/or ultraviolet radiation (e.g., ultraviolet C (UVC) radiation having a wavelength of about 100 to about 280 nm). An antigen composition of the present invention may comprise one, two, three, or more strains of poliovirus. The antigen composition may serve as an improved vaccine to stimulate protective immunity when introduced to a subject by injection or other delivery systems such as those known to those of skill in the art.

A method of the present invention may use an antioxidant and/or antioxidant composition to protect the antigenic epitopes on the surface of a virus while leaving the nucleic acid inside the virus subject to damage and/or destruction from radiation (e.g., ionizing and/or UV radiation).

An antioxidant composition of the present invention may comprise a divalent cation, a peptide, and a buffer system. In some embodiments, the antioxidant composition comprises manganese chloride ($MnCl_2$), a decapeptide (such as, e.g., DEHGTAVMLK [SEQ ID NO:1]) and a phosphate buffer (e.g., a potassium phosphate buffer). Other buffers, such as TRIS, MES, and the like may be substituted for phosphate buffer.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim and/or file any new claim accordingly, including the right to be able to amend any originally filed claim to depend from and/or incorporate any feature of any other claim or claims although not originally claimed in that manner. These and other objects and/or aspects of the present invention are explained in detail in the specification set forth below. Further features, advantages and details of the present invention will be appreciated by those of ordinary skill in the art from a reading of the figures and the detailed description of the preferred embodiments that follow, such description being merely illustrative of the present invention.

Figure 1:
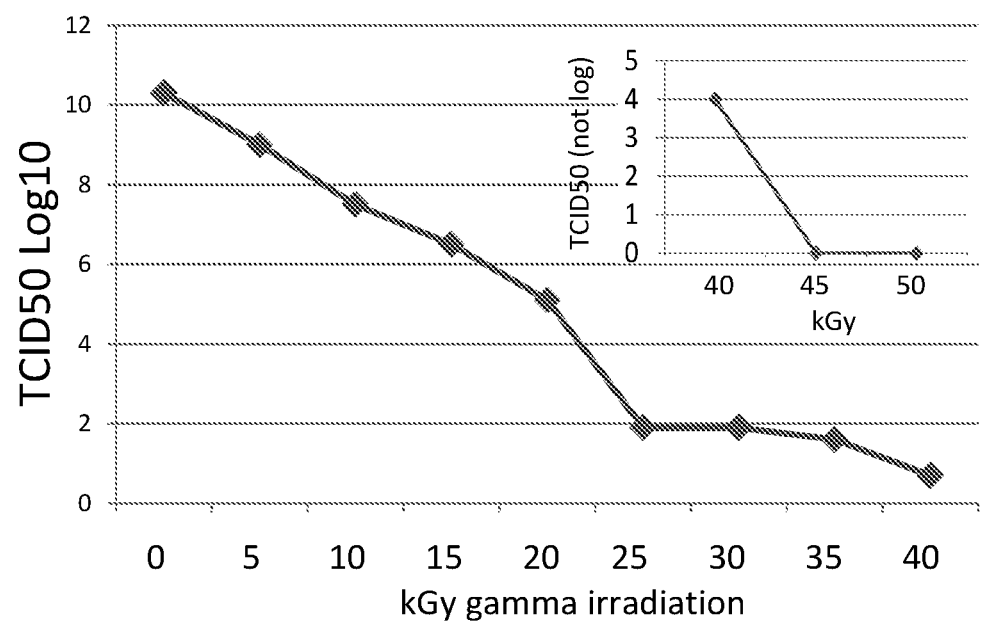
FIG. 1 shows graphs demonstrating a reduction in infectivity of gamma-irradiated poliovirus (PV). 16 micrograms of PV2 Sabin combined with a manganous-decapeptide-phosphate (MDP) complex was exposed to increasing doses of gamma-irradiation and tested for infectivity using a CCID50 assay. The larger graph reports the Log-10 values, the inset graph reports non-log titers showing no infectivity at 45 and 50 kilograys (kGy) of ionizing radiation.

FIGS. 2A-2C show images of different analyses on irradiated PV. In FIGS. 2A & 2B, PV2S was gamma-irradiated with and without Decapeptide (Dp) or $MnCl_2$ ($Mn^{2+}$) as shown. Aliquots were analyzed by Western blot demonstrating that the addition of Dp and $Mn^{2+}$ protects the VP2 capsid protein from damage (FIG. 2A). Similar results were obtained in blots in which VP1 and VP3 were visualized. Analysis of intact viral RNA by reverse transcriptase and then polymerase chain reaction (RT-PCR) shows that the MDP complex does not protect the RNA from damage (FIG. 2B). The blot shows that the addition of Dp and $Mn^{2+}$ protects VP2 from damage. The PCR assay shows that the addition of Dp or $Mn^{2+}$ does not protect the RNA from damage. FIG. 2C shows an electron micrograph of PV1S prior to irradiation (top), gamma-irradiation without Dp or $Mn^{2+}$ (middle) and with Dp and $Mn^{2+}$ (bottom). 91.8% of the un-irradiated particles appear high-density. After gamma-irradiation, 90.0 and 2.0% were of high density in samples with and without MDP, respectively, as determined by counting >700 particles.

FIG. 3 shows Log-2 anti-PV2 neutralization titers of rats immunized with 1×, 01/2×, or reduced human doses of IPOL (circles), VeroPol (squares), or Ir-PV2S (triangles). Ir-IPVS irradiated without the MDP complex was included as a control (stars). Rats were immunized on Days 1 and 21 and bled for test sera on Days 35 (panels A, C, and E) and 49 (panels B, D, and F). Panels A and B show sera from 1× human doses containing 8 DU of PV2 antigens. Panels C and D show sera from 0.5× human doses containing 4 DU of PV2 antigens. Panels E and F show sera from reduced doses of PV2 antigens including ⅛, 1/16, 1/32, or 1/64 of a human dose containing 1, 0.5, 0.25, or 0.125 DU of PV2 antigen, respectively.

FIG. 4 shows graphs of anti-PV1 neutralization titers from rats immunized with irradiated 1× (Panels A, B) or 0.5× (Panels C, D) human dose of Ir-PV1 and licensed IPV vaccines, IPOL (Sanofi) and VeroPol (Staten Serum Institute). Neutralization data presented as Log-2 values from immunization with IPOL (circles), IPV (squares), Ir-PV1 with MDP (triangles) or Ir-PV1 irradiated without MDP (stars) Immunizations were performed on Days 1 and 21, test bleeds for neutralization assays on Days 35 and 49 as shown. Horizontal lines indicate mean neutralization values for each group. BD=Below Detectable limits (<1).

FIG. 5 shows anti-PV1 neutralization titers from rats immunized with UVC-inactivated PV1 Sabin. PV1 Sabin virus was compounded with (top panel) or without (bottom panel) the MDP complex and irradiated for 60 minutes with a UVC light that emits 0.7 $mW/cm^2$. The two inactivated virus preparations were analyzed for D antigen concentration and amounts equal to 1 human dose were used to immunize rats. The rats were immunized on Days 0 and 21 and serum was collected on Day 49. The neutralization titers for each rat sera are shown along with the Log-2 titer and the group means. The sera marked with asterisks exhibited no neutralization at 1:2 dilutions.

FIG. 6 shows anti-PV1 neutralization titers of sera from rats immunized with UVC-inactivated PV1 Sabin. The Log 2 titer for each serum sample shown in FIG. 5 is graphed, the mean values are shown as horizontal lines, and error bars are included. PV1 Sabin was compounded with or without MDP and the infectivity was inactivated by exposure to a UVC light that emits 0.7 $mW/cm^2$ for 60 minutes. Rats were immunized on Days 0 and 21 and test bled for sera on Day 49 with 40 D antigen units of inactivated virus (1× human dose). The sera were analyzed for neutralizing antibody activity in a standard TCID50 assay. Log-2 neutralizing titers are shown for each rat sera in the two groups with MDP (solid symbols) or without MDP (open symbols).

FIG. 7 shows analysis of UVC-irradiated PV3 Sabin virus. Left panel shows infectivity. PV3 Sabin was complexed with (squares) or without (triangles) MDP and exposed to a UVC light that emits 0.7 $mW/cm^2$ for 0, 3, 10, or 30 minutes. The samples were analyzed on an infectivity assay using MRCS cells and the Log-10 TCID50 titer values were graphed. Right panel shows D antigen analysis of the same samples. The D antigen unit per milliliter volume values are shown along with % remaining values.

FIG. 8 shows Anti-PV3 neutralization titers from rats immunized with UVC-inactivated PV3 Sabin on Days 0 and 21 and bled for sera on Day 49. PV3 Sabin virus was compounded with (top panel) or without (bottom panel) the MDP complex and irradiated with a UVC light that emits 0.7 $mW/cm^2$ for 60 minutes. The two inactivated virus preparations were analyzed for D antigen concentration and amounts equal to 2×, 1×, ½×, and ⅛× human dose (64, 32, 16, 8 D antigen units) were used to immunize rats. The rats were boosted 21 days after the initial immunization and serum samples collected 28 days later. The neutralization titers for each rat sera are shown along with the Log-2 titer and the group means.

Figure 9:
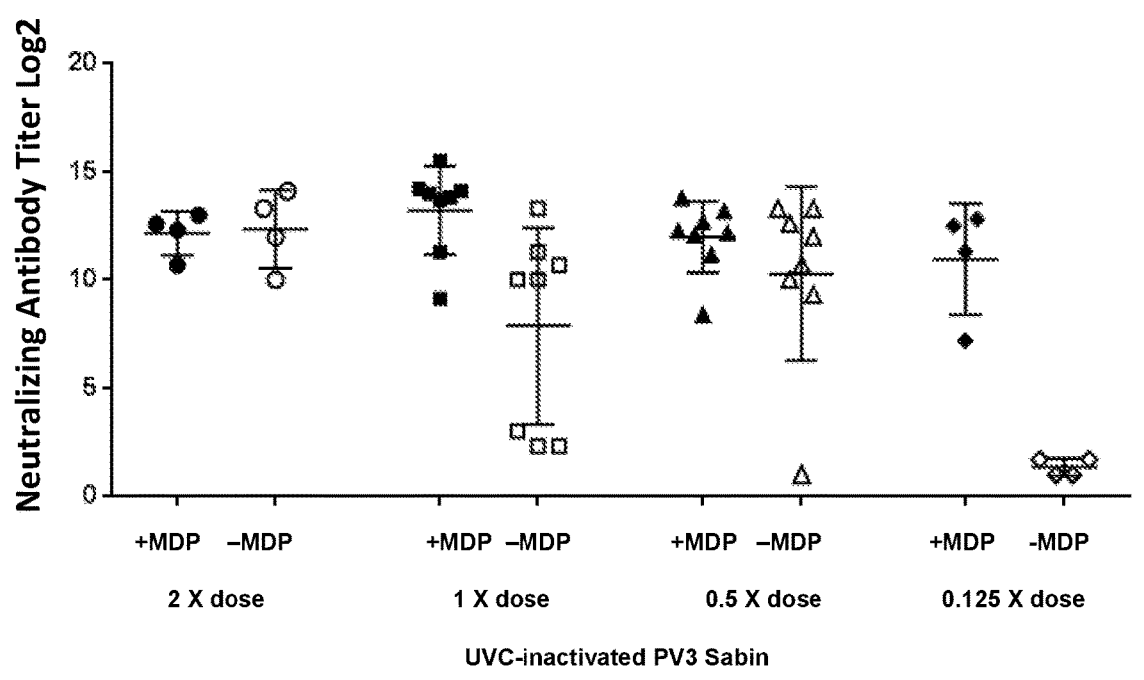

FIG. 9 shows neutralization titers of sera from rats immunized with UVC-inactivated PV3 Sabin. PV3 Sabin was compounded with or without MDP and inactivated by exposure to a UVC light that emits 0.7 $mW/cm^2$ for 60 minutes. Rats were immunized on Day 0 and boosted on Day 21 with 64, 32, 16, or 4 D antigen units of antigen, corresponding to 2× (circles), 1× (squares), 0.5× (triangles), and 0.125× (diamonds) doses, respectively. The Log-2 values of the anti-PV3 neutralization titers from the sera for each animal in the groups are shown. Data from animals immunized with virus compounded with MDP prior to UVC-inactivation are shown as solid symbols while sera from animals immunized with virus compounded without MDP are shown in open symbols. The data suggest that the inclusion of MDP reduces damage to neutralizing epitopes on the virus and this action is more pronounced at lower antigen doses.

DETAILED DESCRIPTION OF THE INVENTION

The present invention is now described more fully hereinafter with reference to the accompanying drawings, in which embodiments of the invention are shown. This invention may, however, be embodied in many different forms and should not be construed as limited to the embodiments set forth herein; rather these embodiments are provided so that this disclosure will be thorough and complete and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a," "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, *In re Herz*, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

The term "about," as used herein when referring to a measurable value such as an amount or concentration and the like, is meant to encompass variations of ±10%, +5%, ±1%, ±0.5%, or even ±0.1% of the specified value as well as the specified value. For example, "about X" where X is the measurable value, is meant to include X as well as variations of ±10%, 5%, ±1%, ±0.5%, or even ±0.1% of X. A range provided herein for a measureable value may include any other range and/or individual value therein.

"Pharmaceutically acceptable" as used herein means that the compound, anion, cation, or composition is suitable for administration to a subject to achieve the treatments described herein without unduly deleterious side effects in light of the severity of the disease and necessity of the treatment.

As used herein, the terms "increase," "increases," "increased," "increasing," "improve," "enhance," and similar terms indicate an elevation in the specified parameter of at least about 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500% or more.

As used herein, the terms "reduce," "reduces," "reduced," "reduction," "inhibit," and similar terms refer to a decrease in the specified parameter of at least about 5%, 10%, 15%, 20%, 25%, 30%, 35%, 40%, 45%, 50%, 55%, 60%, 65%, 70%, 75%, 80%, 85%, 90%, 95%, 97%, or 100%.

The term "sequence identity," as used herein, has the standard meaning in the art. As is known in the art, a number of different programs can be used to identify whether a polynucleotide or polypeptide has sequence identity or similarity to a known sequence. Sequence identity or similarity may be determined using standard techniques known in the art, including, but not limited to, the local sequence identity algorithm of Smith & Waterman, *Adv. Appl. Math.* 2:482 (1981), by the sequence identity alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Drive, Madison, WI), the Best Fit sequence program described by Devereux et al., *Nucl. Acid Res.* 12:387 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351 (1987); the method is similar to that described by Higgins & Sharp, *CABIOS* 5:151 (1989).

Another example of a useful algorithm is the BLAST algorithm, described in Altschul et al., *J. Mol. Biol.* 215:403 (1990) and Karlin et al., *Proc. Natl. Acad. Sci. USA* 90:5873 (1993). A particularly useful BLAST program is the WU-BLAST-2 program which was obtained from Altschul et al., *Meth. Enzymol.*, 266:460 (1996); blast.wustl/edu/blast/README.html. WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., *Nucleic Acids Res.* 25:3389 (1997).

A percentage amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

The alignment may include the introduction of gaps in the sequences to be aligned. In addition, for sequences which contain either more or fewer nucleotides than the polynucleotides specifically disclosed herein, it is understood that in one embodiment, the percentage of sequence identity will be determined based on the number of identical nucleotides in relation to the total number of nucleotides. Thus, for example, sequence identity of sequences shorter than a sequence specifically disclosed herein, will be determined using the number of nucleotides in the shorter sequence, in one embodiment. In percent identity calculations relative weight is not assigned to various manifestations of sequence variation, such as insertions, deletions, substitutions, etc.

In one embodiment, only identities are scored positively (+1) and all forms of sequence variation including gaps are assigned a value of "0," which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

"Immunogen" and "antigen" are used interchangeably herein and refer to a molecule that elicits a specific humoral and/or cellular-mediated immune response, for example, an immune response in which an antibody is stimulated and binds to the molecule or virus. The binding site for an antibody within an antigen and/or immunogen may be referred to as an epitope (e.g., an antigenic epitope).

As used herein, "D antigen content" refers to the combined activity of multiple immunostimulatory poliovirus epitopes. Early studies of poliovirus virulence described two distinct antigenic forms of poliovirus classified as non-infectious empty particles and/or virus of low infectivity comprising "C" antigen, and infectious viruses comprising "D" antigen, which could be inactivated and converted to C antigen by heating at 56° C. The D antigen assay, e.g., an ELISA assay comprising antibodies reactive to D antigen content (e.g., epitope(s) of infectious virus), is a measure of antigenicity and has been used to predict the immunogenicity of vaccine preparations, wherein a higher D antigen content correlates with higher immunogenicity.

A vaccine is an immunogen that is used to generate an immunoprotective response, e.g., by priming the immune system such that upon further exposure to an antigen (e.g., an immunogen and/or antigen of an infectious entity such as, e.g., an infectious virus) the immune response is more protective to the host (e.g., vaccine recipient, e.g., the subject) as compared to the immune response against exposure to the antigen without prior vaccination. For example, an induced antibody can be provided by a vaccine that reduces the negative impact of the immunogen found on an infectious virus, or entity expressing same, in a host. The dosage for a vaccine may be derived, extrapolated, and/or determined from preclinical and clinical studies, as known to those of skill in the art. Multiple doses of a vaccine may be administered as known in the art and/or may be administered as needed to ensure a prolonged prophylactic and/or anamnestic (memory) state (e.g., a primed state). In some embodiments, the successful endpoint of the utility of a vaccine for the purpose of this invention is the resulting presence of an induced immune response (e.g., humoral and/or cell-mediated) resulting, for example, in the production of serum antibody or antibodies made by the host which recognizes the intended antigen. Such antibodies can be measured as is known in the art by a variety of assays such as, e.g., antivirus neutralization assays of serum sampled from animals or humans immunized with said vaccine and/or immunogen.

As used herein, the term "antigen-sparing" and/or "dose-sparing" refer to an effect whereby the amount of immunogen/antigen used in a vaccine and/or the amount of vaccine given may be reduced without adversely affecting the protective nature of the induced immunoprotective response in the vaccine recipient such as, for example, without affecting the effectivity, quality, and/or protection from disease of the induced immunoprotective response in the vaccine recipient.

Polioviruses are non-enveloped viruses containing positive-sense genomic RNA and exist as three antigenically distinct serotypes: Types 1, 2, and 3 (i.e., PV1, PV2, and PV3). Polioviruses are members of the genus Enterovirus of the family Picornaviridae and replicate in the gastrointestinal tract. At a relatively low frequency, the virus infects neurological tissues where it can cause temporary paralysis, permanent paralysis, or death. Because polioviruses have less water than enveloped viruses such as influenza and Venezuelan Equine Encephalitis Virus (VEEV), higher doses of ionizing radiation are typically required for inactivation of infectivity.

The two general types of poliovirus vaccines that have been used since their approvals in the 1950s are the inactivated polio vaccine (IPV) and the oral live-attenuated (non-inactivated) polio vaccine (OPV). IPV was originally developed by Jonas Salk and colleagues and is manufactured by the propagation and purification of neuropathogenic strains of polioviruses Type 1, 2, and 3 followed by chemical inactivation of infectivity using formaldehyde and subsequent purification. IPV is typically administered by intramuscular injection without the use of adjuvants and stimulates systemic immunity which protects the host from neuropathogenic disease. OPV is manufactured by the propagation and purification of strains of the three serotypes that have been attenuated for pathogenesis. The attenuated strains, originally developed by Albert Sabin and colleagues are termed "Sabin" strains. As a live attenuated virus vaccine that is administered orally, OPV replicates in the intestines and stimulates both gut and systemic immunity from infection and/or disease. Both IPV and OPV have been used to control poliovirus infection and the incidence of poliomyelitis. The vaccines have contributed to the eradication of poliomyelitis in all except a small number of countries.

In the years between 2005 and 2015, it is estimated that more than 10 billion doses of OPV have been administered to over 2.5 billion children and prevented more than 10 million cases of polio infection. In some cases, the OPV vaccine can lose its disease-attenuation phenotype during replication in the gut and lead to the excretion of neuropathogenic virus in the stools. The progeny virus can infect inadequately vaccinated bystanders exposed to the infected stool. In addition, inadequately treated sewage can result in contamination of water bodies which can also lead to infection of inadequately vaccinated people. During past years when thousands, if not hundreds of thousands, of people developed polio diseases through contact with wild-type poliovirus strains, the relatively low rate of reversion of the OPV was a less significant health hazard in the population than was the risk of natural infection. In contrast, as eradiation is completed or is almost completed in defined geographical areas and, eventually, the global population, the incidence of disease caused by vaccine revertants becomes more significant and problematic. In 2017, there were 22 reported cases of polio infection, down from approximately 350,000 in 1988. Because there are approximately 200 asymptomatic cases for every case of paralytic polio, the incidence of virus circulating in the population is greater than the number reported. In countries where the three polio serotypes have been eradicated for many years, the OPV has been replaced with IPV to prevent cases of vaccine-associated infection and disease.

IPV also has deficiencies. The vaccine is produced using neuropathogenic strains. The production and handling of large quantities of neuropathogenic strains requires a high level of biological containment to prevent the accidental release of virus from the production facilities. Published reports document such accidental releases of virus into the neighboring environment for more than one production facility. The World Health Organization has certified that PV2 has been eradicated and no cases of infection or disease from wild-type PV2 virus have been reported in recent years. There have been no reported cases of PV3 infection since 2012 and the world health community anticipates that PV1 will be eradicated in the near future. Upon eradication, the use of large quantities of neuropathogenic strains will become an increasing biohazard risk. Years after the eradication has been accomplished and the mass immunization against poliovirus begins to wane in many countries, accidental or purposeful escape of neuropathogenic poliovirus could undo the enormous efforts expended to eradicate the three viruses. For this reason, the replacement of neuropathogenic strains by attenuated Sabin strains would reduce the biohazards associated with the manufacture of IPV. Published reports document that the dominant epitope in the VP1 capsid protein of PV1-Sabin is damaged by formaldehyde treatment. Although some countries have licensed the use of formaldehyde-inactivated Sabin strains as IPV vaccines, concerns regarding its ability to induce durable protective immunity remain.

The potency of a poliovirus vaccine or immunogen can be measured by analysis of the neutralizing antibody activity in immunized humans or selected test animals, wherein higher quantification of neutralizing antibody (e.g., IgA, IgM and/or IgG, e.g., IgG1, IgG2, IgG3, and/or IgG4) activity in immunized subjects (e.g., humans and/or test animals) correlates with improved immunoprotective responses in subsequent exposure to wildtype poliovirus. In the neutralization assay, diluted serum samples are mixed with standardized quantities of PV1, -2, and/or -3 and allowed to form antibody-virus complexes. The mixture is then applied to monolayers of mammalian cells, such as HeLa, Vero and/or MRCS cell lines, to permit infectious virus to attach to the cells. Typically, the assay is conducted in tissue culture plates having multiple wells (48, 96, or 386 wells per plate) using multiple well replicates for each serum-virus test. The inocula are washed off with a standard buffer, growth media is added to the cells, and the culture plates are incubated from about 35° C. to about 37° C. to allow virus growth and multiple replication cycles. The wells are scored 3-6 days later as infected or uninfected to determine whether the serum inhibited virus infection of the monolayers (e.g., via the neutralizing antibodies within the serum). The virus neutralization titer is expressed as the reciprocal of the dilution of serum that causes a reduction of 50% of infected wells among the replicate wells, e.g., a dilution of 1:2, 1:4, 1:6, 1:8, 1:10, 1:12, etc., that causes a reduction of 50% of infected wells would correspond to a virus neutralization titer of 2, 4, 6, 8, 10, 12, etc., respectively, wherein a higher neutralization titer is more effective at providing protection. A virus neutralization titer of 8, corresponding to a 1:8 dilution of serum, is generally accepted as a correlate of protection in humans. A titer of 8 is equivalent to a Log-2 titer of 3. Thus, if a vaccine containing a reduced mass of antigen stimulates equivalent or greater neutralization titers as compared to a reference vaccine (e.g., a current commercial (e.g., formalin/formaldehyde) inactivated poliovirus immunogen, e.g., IPV), then it is considered to be "antigen-sparing."

Immunization of Wistar rats is a common test animal model for predicting the potency of vaccines. A vaccine antigen that stimulates a neutralization titer of 8 in the super-majority of immunized rats correlates to protection in humans.

Provided according to embodiments of the present invention are irradiation-inactivated poliovirus immunogens. The irradiation-inactivated antigens of the present invention can stimulate neutralizing antibodies in the standard Wistar rat model which correlates closely with protective immunity in immunized humans. An irradiation-inactivated poliovirus immunogen of the present invention may stimulate protective immunity in a human (e.g., a human immunized with the immunogen).

A composition of the present invention may comprise one or more different irradiation-inactivated poliovirus immunogens such as, for example, one or more (e.g., 1, 2, 3, 4, 5 or more) attenuated and/or neuropathogenic Sabin strain(s). In some embodiments, a composition of the present invention may comprise one or more attenuated S19 strain(s). A composition of the present invention may comprise a pharmaceutically acceptable carrier. In some embodiments, a composition of the present invention is a vaccine. In some embodiments, provided is an inactivated trivalent whole virus composition, which may replace the currently licensed OPV and IPV vaccines.

An irradiation-inactivated poliovirus immunogen of the present invention may stimulate neutralizing antibodies in a subject (e.g., an immunized human), optionally with a virus neutralizing titer of about 8 or more (e.g., about 8, 10, 25, 50, 80, 100, 300, 500, 800, 1,000, 2,000, 3,000, 4,000, 5,000, 6,000, 7,000, 8,000, 9,000, 10,000, 12,000, 14,000, 16,000, 20,000 or more, and/or any value or range therein). For example, in some embodiments an irradiation-inactivated poliovirus immunogen of the present invention may stimulate neutralizing antibodies in a subject with a virus neutralizing titer of about 8 to about 20,000; about 100 to about 15,000; about 1,000 to about 10,000, or about 15,000 to about 20,000.

According to some embodiments of the present invention, provided is a method for producing an inactivated poliovirus vaccine, which may comprise one or more (e.g., 1, 2, 3, 4, 5 or more) attenuated and/or neuropathogenic Sabin strain(s). Instead of using formaldehyde, which can damage neutralizing epitopes and require lengthy incubations of 2 weeks or longer, a method of the present invention may comprise using ionizing (e.g., gamma) and/or ultraviolet (e.g., UVC) irradiation to inactivate viral infectivity. In some embodiments, the ionizing irradiation may be gamma irradiation. In some embodiments, the ultraviolet irradiation may be ultraviolet C (UVC) irradiation.

In some embodiments, a method of the present invention comprises providing an antioxidant composition (e.g., a composition comprising a peptide such as, e.g., a manganese-decapeptide-phosphate (MDP) composition) comprising a complex, which may protect poliovirus epitopes during irradiation (e.g., supralethal irradiation). An antioxidant composition of the present invention may comprise a divalent cation (e.g., $Mn^{2+}$), a peptide, and a buffer system. In some embodiments, the antioxidant composition comprises manganese chloride ($MnCl_2$), a decapeptide, and a phosphate buffer. In some embodiments, the antioxidant composition comprises manganese chloride ($MnCl_2$), a decapeptide, and a Tris buffer. In some embodiments, the antioxidant composition comprises manganese chloride ($MnCl_2$), a decapeptide, and an MES buffer. In some embodiments, an antioxidant composition of the present invention comprises a manganese-decapeptide-phosphate (MDP) complex.

A method of the present invention may use an antioxidant and/or antioxidant composition to protect the antigenic epitopes on the surface of a virus while leaving the nucleic acid inside the virus subject to damage and/or destruction from ionizing radiation (e.g., gamma radiation) and/or UV radiation (e.g., UVC radiation).

A peptide of the present invention may comprise a 2 or more amino acids (e.g., 2, 3, 4, 5, 6, 7, 8, 9, 10, 11, 12, 13, 14, 15, 16, 17, 18, 19, 20, or more), optionally wherein the peptide comprises two or more amino acids residues from the sequence DEHGTAVMLK (SEQ ID NO:1) in any order and/or length. The exact sequence and/or length of the peptide may vary and the peptide may contribute to antioxidant activities and/or function as an antioxidant in a composition of the present invention. For example, in some embodiments the peptide may be a quadripeptide (4mer), a pentapeptide (5mer), a hexapeptide (6mer), a heptapeptide (7mer), an octapeptide (8mer), a nonapeptide (9mer), and/or a decapeptide (1 Omer). In some embodiments, a peptide (e.g., a decapeptide) of the present invention may comprise the amino acids DEHGTAVMLK (SEQ ID NO:1) in any order and/or length, e.g., the peptide may comprise the sequence of amino acids HMLK (SEQ ID NO:2), a scrambled sequence of the amino acids HMLK (SEQ ID NO:2), the sequence of amino acids HMHMHM (SEQ ID NO:3), a scrambled sequence of the amino acids HMHMHM (SEQ ID NO:3), the sequence of amino acid DEHGTAVMLK (SEQ ID NO:1), and/or a scrambled sequence of the amino acids DEHGTAVMLK (SEQ ID NO:1). In some embodiments, a peptide may comprise an amino acid sequence having at least about 5%, 10%, 15%, 20%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% sequence identity to the amino acid sequence DEHGTAVMLK (SEQ ID NO:1). In some embodiments, a peptide may comprise an amino acid sequence having at least about 5%, 10%, 15%, 20%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% sequence identity to the amino acid sequence HMLK (SEQ ID NO:2). In some embodiments, a peptide may comprise an amino acid sequence having at least about 5%, 10%, 15%, 20%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% sequence identity to the amino acid sequence HMHMHM (SEQ ID NO:3).

In some embodiments, an antioxidant composition of the present invention may comprise a peptide in a concentration of about 0.5 mM to about 10 mM, e.g., about 0.5, 1, 1.5, 2, 2.5, 3, 3.5, 4, 4.5, 5, 5.5, 6, 6.5, 7, 7.5, 8, 8.5, 9, 9.5, or 10 mM, or any value or range therein. For example, in some embodiments an antioxidant composition of the present invention may comprise, for example, a peptide in an amount of about 2.5 mM to about 5 mM, about 0.7 to about 3.7 mM, or about 2 mM to about 8 mM. In some embodiments, an antioxidant composition of the present invention may comprise a peptide in an amount of about 3 mM, for example, about 3 mM of a decapeptide.

In some embodiments, an antioxidant composition of the present invention may comprise a divalent cation, such as, e.g., manganous $Mn^{2+}$. In some embodiments, the divalent cation may be provided as a salt, e.g., $MnCl_2$. In some embodiments, an antioxidant composition of the present invention may comprise a divalent cation (e.g., $Mn^{2+}$) in a concentration of about 1 mM to about 10 mM, e.g., about 1, 1.5, 2, 2.5, 3, 3.5, 4, 4.5, 5, 5.5, 6, 6.5, 7, 7.5, 8, 8.5, 9, 9.5, or 10 mM, or any value or range therein. For example, in some embodiments, an antioxidant composition of the present invention may comprise $Mn^{2+}$ in an amount of about 1.4 mM to about 5.3 mM, about 2 mM to about 7 mM, or about 1 mM to about 9.8 mM. In some embodiments, an antioxidant composition of the present invention may comprise about 3 mM $Mn^{2+}$. In some embodiments, an antioxidant composition of the present invention may comprise about 3 mM $MnCl_2$.

In some embodiments, an antioxidant composition of the present invention may comprise a buffer, e.g., a phosphate buffer, a Tris buffer, an MES buffer, a HEPES buffer, and/or the like. In some embodiments, the buffer may be in a concentration of about 10 mM to about 500 mM, e.g., about 10, 15, 20, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, 450, 495, 496, 497, 498, 499, or 500 mM, or any value or range therein. For example, in some embodiments, an antioxidant composition of the present invention may comprise about 20 mM to about 100 mM phosphate buffer, about 10 mM to about 200 mM phosphate buffer, or about 40 mM to about 120 mM phosphate buffer. In some embodiments, an antioxidant composition of the present invention may comprise about 50 mM phosphate buffer. In some embodiments, the buffer and/or antioxidant composition may have a pH of about 5 to about 9, or any value or range therein, e.g., about 6.8 or about 7.4. In some embodiments, an antioxidant composition of the present invention and/or method of their use may comprise a composition and/or method as described in PCT/US2008/073479; PCT/US2011/034484; and/or PCT/US2012/062998, the disclosures of which are incorporated herein by reference.

In some embodiments, an antioxidant composition of the present invention comprises $MnCl_2$ in a concentration of about 1 mM to about 10 mM, a decapeptide (e.g., DEHGTAVMLK [SEQ ID NO:1]) in a concentration of about 0.5 mM to about 10 mM, and a phosphate buffer in a concentration of about 10 mM to about 500 mM. In some embodiments, an antioxidant composition of the present invention comprises about 3 mM $MnCl_2$, about 3 mM decapeptide (e.g., DEHGTAVMLK [SEQ ID NO:1]), and about 200 mM phosphate buffer. However, concentrations of the components in the antioxidant composition may be varied as long as there is little degradation of effectiveness. An antioxidant composition may further comprise one or more excipient(s) such as, e.g., sorbitol, trehalose, etc., and/or one or more peptide(s) such as, e.g., HMHMHM (SEQ ID NO:3), HMLK (SEQ ID NO:2), and/or the like.

A method of the present invention may expose a virus present in an antioxidant composition to radiation (e.g., ionizing (e.g., gamma) radiation and/or ultraviolet (e.g., UVC) radiation), which may result in protection of one or more epitopes (e.g., surface protein epitope(s), e.g., VP1, VP2, VP3, and/or VP4 epitope(s)) while leaving the viral genome open to damage and/or destruction from the radiation. In some embodiments, a virus is exposed to ionizing radiation (e.g., gamma rays and/or x-rays) in an amount of at least about 10, 15, 20, 25, 30, 35, 40, 45, 50, 55, or 60 kGy. In some embodiments, a virus is exposed to ionizing radiation (e.g., gamma radiation) in an amount of about 30, 35 or 40 kGy to about 45 or 50 kGy. In some embodiments, a virus is exposed to UV (e.g., UVC) radiation in an amount of about 0.01, 0.5, or 0.1 $kJ/m^2$ to about 5, 10, or 15 $kJ/m^2$ (e.g., about 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, or 15 $kJ/m^2$), or an equivalent derived exposure time, surface area and/or light source wavelength and/or wattage. In some embodiments, a poliovirus is exposed for about 60 minutes to a UVC light source emitting about 0.7 mW/cm² (e.g., in a thick-walled plastic tube) and/or a poliovirus is exposed for about 1, 5, 10, or 30 seconds to about 1, 1.5, or 2 minutes to a UVC light source emitting about 5 mW/cm², optionally when the poliovirus is contained in a UV-transparent (e.g., thin-walled) vessel or tube. In some embodiments, a poliovirus is exposed to a UV source (e.g., a UVC light source) having an intensity and/or for a period of time sufficient to inactivate the infectivity.

Due to the low concentration of water and lipids in non-enveloped viruses, non-enveloped viruses typically require higher doses of radiation than, for example, influenza and VEEV, for inactivation, which causes increased damage to protein antigens. In some embodiments, a composition and/or method of the present invention has and/or provides improved protection of one or more surface epitope(s).

In some embodiments, a method of the present invention replaces air and/or dioxygen in contact with a composition of the present invention with argon. For example, the air in tubes comprising the virus and antioxidant composition may be at least partially replaced with argon. In some embodiments, a method of the present invention reduces the concentration and/or removes metals such as, e.g., iron, from compositions comprising the virus and/or antioxidant composition. For example, the amount of trace iron contamination in phosphate buffers and other reagents may lead to increased oxidative damage of protein epitopes. Thus, in some embodiments, iron and/or other metals may be removed from buffers and water using methods known to those of skill in the art such as, e.g., by passage through a chelating chromatographic column (Chelex column, Bio-Rad). In some embodiments, iron and/or other metals may be present in a concentration less than about 100 mM.

Provided according to some embodiments of the present invention is increased protection of poliovirus epitopes (e.g., surface protein epitopes) from damage during the irradiation process (e.g., ionizing and/or ultraviolet irradiation) compared to current commercial (e.g., formalin/formaldehyde) inactivated poliovirus immunogens (e.g., such as but not limited to IPV). In some embodiments, the current commercial inactivated poliovirus immunogen(s) include, but are not limited to, IPV (e.g., IPOL and/or VeroPol). Increased protection of poliovirus epitopes may be compared to a control, e.g., increased protection of epitopes during gamma and/or UVC irradiation inactivation as compared to formalin/formaldehyde inactivation. Increased protection may be accomplished by at least partially replacing ambient air with a non-reactive gas (e.g., argon) in containers (e.g., tubes) containing the virus and/or removing and/or decreasing the amount of iron in compositions comprising the pre-inactivated virus. In some embodiments, air may be at least partially replaced with a non-reactive gas (e.g., argon). In some embodiments, air may be at least partially replaced with a non-reactive gas such that the content of oxygen is reduced by about 50% or more such as, e.g., by about 50%, 55%, 60%, 65%, 70%, 75%, 80%, 85%, 90%, 95%, 96%, 97%, 98%, 99% or more compared to the content of oxygen in the atmosphere and/or prior to the at least partial replacement.

Ultraviolet light may be used to inactivate poliovirus with minimal to no damage to epitopes that stimulate neutralizing antibodies (e.g., antibodies against viral surface protein epitopes). Ultraviolet light can be divided into categories based on wavelength. UVA is 315-400 nm, UVB is 280-315 nm, and UVC is 100-280 nm. The infectivity of poliovirus may be completely inactivated when exposed to a UVC (e.g., comprising a wavelength of about 220 to about 280 nm) light source emitting about 0.7 mW/cm² for about 60 minutes (e.g., in a thick-walled plastic tube) or a UVC light source emitting about 5 mW/cm² for about 1, 5, 10, or 30 seconds to about 1, 1.5, or 2 minutes if the poliovirus is contained in a UV-transparent (e.g., thin-walled) vessel or tube.

As described herein, a method of the present invention may comprise exposing a poliovirus to radiation (e.g., ionizing and/or UV radiation) and the poliovirus may be present in a vessel (e.g., a tube or container). As one of skill in the art would understand, the exposure conditions (e.g., intensity of radiation and/or time of exposure) may vary depending on the type and/or properties of the vessel. Suitable vessel properties (e.g., thickness and transparency) for exposure to and/or penetrance by radiation (e.g., UVC) can be selected based on the radiation conditions (e.g., radiation source and intensity) and/or the exposure conditions can be modified based on the vessel. For example, in some embodiments, a vessel and/or tube may be clear and/or transparent, or may be opaque and/or frosted. In some embodiments, a vessel or tube may have a thickness of about 1 mm or more (e.g., about 1, 1.25, 1.5, 1.75, 2, 2.25, 2.5, 2.75, or 3 mm or more) (e.g., a "thick-walled" tube or vessel). In some embodiments, a vessel or a tube may have a thickness of about less than 1 mm (e.g., about 0.05, 0.1, 0.15, 0.2, 0.25, 0.30, 0.35, 0.40, 0.45, 0.50, 0.55, 0.60, 0.65, 0.70, 0.75, 0.80, 0.85, 0.90, or 0.95 mm) (e.g., a "thin-walled" tube or vessel). In some embodiments, a method of the present invention may comprise exposing an immunogen of the present invention to radiation while the immunogen is flowing in and/or being transported through a vessel and/or tube (e.g., a flow cell).

Thus, in some embodiments, a method of the present invention may expose a poliovirus, optionally in a UV-transparent vessel or tube, to ultraviolet light (e.g., UVC) in an amount sufficient to at least partially inactivate the infectivity of the poliovirus. In some embodiments, an amount sufficient to inactivate the poliovirus may be a wavelength of about 220 to about 280, e.g., about 220, 225, 230, 235, 240, 245, 250, 255, 260, 265, 270, 275, or 280, or any range or value therein. In some embodiments, an amount sufficient to inactivate the poliovirus may be a UVC light source emitting about 0.5 mW/cm² to about 10 mW/cm², e.g., about 0.5, 0.75, 1, 1.25, 1.5, 1.75, 2, 3, 4, 5, 6, 7, 8, 9, or 10 mW/cm² or any value or range therein. In some embodiments, an amount sufficient to inactivate the poliovirus may be a UVC light source exposure for about 10 seconds to about 75 minutes, e.g., about 0.05, 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, or 75 minutes, or any value or range therein. For example, in some embodiments, a method of the present invention may comprise exposing a poliovirus to UVC in an amount sufficient to completely inactivate the poliovirus, e.g., about 60 minutes of exposure to a UVC light source at wavelength of about 254 emitting about 0.7 mW/cm², or about 10 seconds to 5 minutes of exposure to a UVC light source at wavelength of about 254 emitting about 5 mW/cm² e.g., in a UVC-transparent tube or vessel. In some embodiments, when complexed with an MDP complex during UVC-inactivation, poliovirus epitopes are protected from damage as evidenced by stimulation of neutralizing antibodies.

In some embodiments, a method of the present invention comprises pre-treating a composition comprising a virus and optionally a MDP composition with ultraviolet (UV) light (e.g., UVC) and then with ionizing radiation.

The sterilizing effects of x-rays and/or gamma-rays in vaccine production are a result of direct damage to proteins and nucleic acids by photons and, more significantly (by far), indirect damage caused by reactive oxygen species (ROS) generated from the radiolysis of water molecules.

Some embodiments of the present invention result in protection of all or at least a portion (e.g., 10% or more, e.g., about 10%, about 20%, about 30%, about 40%, about 50%, about 60%, about 70%, about 80%, about 90%, about 95%, about 96%, about 97%, about 98%, or about 99% or more) of the exterior proteins that form the epitopes of the virus while leaving the RNA genome susceptible to destruction.

The MDP complex was developed from the long-term study of radio-resistant bacteria. *Deinococcus radiodurans* is exceptionally resistant to oxidation and can survive both desiccation and 12-16 kGy of gamma irradiation (1 kGy=100,000 rads) (Daly et al., 2010; Daly et al., 2004). The resistance to radiation in *Deinococcus radiodurans* is directly related to the concentration of $Mn^{+2}$-peptide-orthophosphate complexes in the cytosol. This antioxidant component has been recapitulated using $MnCl_2$, the decapeptide DEHGTAVMLK (SEQ ID NO:1) (which may be synthetically produced), and phosphate buffer (pH 7.2). A MDP complex of the present invention may protect the structural integrity of antigens at doses of radiation that abolish infectivity. Studies have been published demonstrating the protective effects of MDP and its use in protecting antigenic proteins with VEEV, Chickungunya virus, and *Staphylococcus aureus* (MRSA) (Dabral et al., 2014; Gaidamakova et al., 2012; Honnald et al., 2014). The inventors of the present invention discovered that MDP compositions may be used to prepare irradiation-inactivated attenuated and/or neuropathogenic Sabin strains of poliovirus, which is a picornavirus and therefore not enveloped. The methods of the present invention can be highly scalable. In some embodiments, the immunogens of the present invention are not subjected to inactivation of epitopes as the PV1-Sabin is during formalin-inactivation as evidenced by D antigen content.

In some embodiments, a method of the present invention provides and/or a composition of the present invention comprises an improved antigen as compared to existing poliovaccines. Unlike the OPV, an irradiation-inactivated vaccine (Ir-PV) of the present invention does not replicate and cannot genetically evolve into a pathogenic virus. In addition, unlike the present licensed IPV vaccines, the Ir-PV is produced using attenuated and/or neuropathogenic Sabin strains of the virus and, therefore, leads to reduced biohazards associated with producing and handling large quantities of pathogenic strains.

The irradiation-inactivated polio immunogens of the present invention may be formulated as a trivalent mixture containing varying amounts of the three components, irradiated-poliovirus Type 1 Sabin (Ir-PV1S), irradiated-poliovirus type 2 Sabin (Ir-PV2S), and irradiated-poliovirus Type 3 Sabin (Ir-PV3S). In some embodiments, a composition of the present invention may comprise about 2 to about 50 D antigen units of Ir-PV1S (e.g., about 2, 5, 10, 15, 20, 25, 30, 35, 40, 45, 46, 47, 48, 49, or 50 D antigen units of Ir-PV1S or any value or range therein), about 0.1 to about 10 D antigen units of Ir-PV2S (e.g., about 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 9.6, 9.7, 9.8, 9.9, or 10 D antigen units of Ir-PV2S or any value or range therein), and/or about 5 to about 50 D antigen units of Ir-PV3S (e.g., about 5, 10, 15, 20, 25, 30, 35, 40, 45, 46, 47, 48, 49, or 50 D antigen units of Ir-PV3S or any value or range therein). Alternatively, monovalent compositions comprising a single serotype or bivalent compositions comprising two serotypes may be formulated. In some embodiments, the D antigen content of an irradiation-inactivated polio immunogen of the present invention is reduced by less than about 50% (e.g., by less than about 1%, 2%, 3%, 4%, 5%, 10%, 15%, 20%, 25%, 30%, 35%, 40%, 45%, or 50%) as compared to the D antigen content of purified virus prior to inactivation. For example, in some embodiments, the D antigen content of the irradiation-inactivated polio immunogen is reduced by e.g., less than about 40%, less than about 25%, or less than about 7% compared to the D antigen content of purified virus prior to inactivation.

The irradiation-inactivated polio immunogens may be formulated in a simple solution such as water, a standard buffer, a standard saline solution, and/or the like. In some embodiments, an adjuvant may be included in a composition of the present invention, which may augment the magnitude and/or extend the duration of the immune response.

In some embodiments, a poliovirus immunogen of the present invention may stimulate neutralizing antibodies (e.g., a neutralizing antibody titer of about 8, 10, 25, 50, 80, 100, 300, 500, 800, 1,000, 2,000, 3,000, 4,000, 5,000, 6,000, 7,000, 8,000, 9,000, 10,000, 12,000, 14,000, 16,000, 20,000 or more, and/or any value or range therein), optionally as determined in the standard Wistar rat model. In some embodiments, a poliovirus immunogen of the present invention may stimulate a substantially similar amount (e.g., ±5%, 10%, 15%, or 20%) of neutralizing antibodies as a current commercial poliovaccine (e.g., IPV and/or OPV), optionally as determined in the standard Wistar rat model. In some embodiments, a poliovirus immunogen of the present invention may stimulate an increased amount (e.g., about 2-fold, 3-fold, 4-fold, 5-fold, 6-fold, 7-fold, 8-fold, 9-fold, 10-fold, or more, or, e.g., about $2\text{-}\log_2$, $3\text{-}\log_2$, $4\text{-}\log_2$, $5\text{-}\log_2$, $6\text{-}\log_2$, $7\text{-}\log_2$, $8\text{-}\log_2$, $9\text{-}\log_2$, $10\text{-}\log_2$, or more) of neutralizing antibodies than a current commercial poliovaccine (e.g., IPV and/or OPV), optionally as determined in the standard Wistar rat model. For example, in some embodiments, a poliovirus immunogen of the present invention (e.g., irradiated poliovirus serotype 1, 2, and/or 3) may stimulate neutralizing antibodies in an amount that is within ±20% or less of the amount of neutralizing antibodies provided by a current commercial poliovaccine (e.g., IPV and/or OPV). In some embodiments, a poliovirus immunogen of the present invention (e.g., irradiated poliovirus serotype 1, 2, and/or 3) stimulates neutralizing antibodies in an amount that is at least about 2-fold greater than the amount of neutralizing antibodies provided by a current commercial poliovaccine (e.g., IPV and/or OPV). In some embodiments, a poliovirus immunogen of the present invention (e.g., irradiated poliovirus serotype 1, 2, and/or 3) stimulates neutralizing antibodies in an amount that is at least about $2\text{-}\log_2$ greater than the amount of neutralizing antibodies provided by a current commercial poliovaccine (e.g., IPV and/or OPV).

The use of an irradiation-inactivated poliovirus of the present invention may provide and/or allow for a reduction in the amount of antigen contained in one immunization dose to effect dose-sparing and, thereby, may permit the production of larger numbers of doses per unit of purified starting virus in the manufacturing process. In some embodiments, a dose of a poliovirus antigen of the present invention for one or more of the three serotypes may be reduced such as, e.g., by at least about 5%, 10%, 15%, 20%, 25%, 30%, 35%, 40%, 45%, 50%, 55%, 60%, 65%, 70%, 75%, 80%, 85%, 90%, 95%, 97%, 98%, 99%, or more, optionally as defined by D antigen content for a current commercial IPV vaccine (e.g., IPOL and/or VeroPol). For example, in some embodiments, a dose of a poliovirus antigen of the present invention for serotype 1, 2, and/or 3 may be reduced to ½, ¼, ⅛, ¹⁄₁₆, ¹⁄₃₂, or less of a normal human dose as currently defined by D antigen content and/or by mass (e.g., in micrograms). In some embodiment, a composition (e.g., vaccine) of the present invention comprises an irradiation inactivated PV1 serotype having a D antigen content of less than 40 D antigen units, an irradiation inactivated PV2 serotype having a D antigen content of less than 8 D antigen units, and/or an irradiation inactivated PV3 serotype having a D antigen content of less than 32 D antigen units. For example, in some embodiments, a composition (e.g., vaccine) of the present invention may comprise an irradiation inactivated PV1 serotype having a D antigen content of about 0.1, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 D antigen units, an irradiation inactivated PV2 serotype having a D antigen content of about 0.1, 1, 2, 3, 4, 5, 6, 7, or 8 D antigen units, and/or an irradiation inactivated PV3 serotype having a D antigen content of about 0.1, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 D antigen units. In some embodiments, a composition of the present invention comprises an irradiation inactivated PV1 serotype having a D antigen content of 40 D antigen units, an irradiation inactivated PV2 serotype having a D antigen content of 8 D antigen units, and/or an irradiation inactivated PV3 serotype having a D antigen content of 32 D antigen units. In some embodiments, a composition of the present invention comprises an irradiation inactivated PV1 serotype having a D antigen content of 20 D antigen units, an irradiation inactivated PV2 serotype having a D antigen content of 8 D antigen units, and/or an irradiation inactivated PV3 serotype having a D antigen content of 32 D antigen units. In some embodiments, a composition of the present invention comprises an irradiation inactivated PV1 serotype having a D antigen content of 40 D antigen units, an irradiation inactivated PV2 serotype having a D antigen content of 2 D antigen units, and/or an irradiation inactivated PV3 serotype having a D antigen content of 32 D antigen units. In some embodiments, a composition of the present invention comprises an irradiation inactivated PV1 serotype having a D antigen content of 40 D antigen units, an irradiation inactivated PV2 serotype having a D antigen content of 8 D antigen units, and/or an irradiation inactivated PV3 serotype having a D antigen content of 18 D antigen units. In some embodiments, a composition (e.g., vaccine) of the present invention comprises an irradiation inactivated PV1 serotype, PV2 serotype, and/or PV3 serotype having a D antigen content that reduced by about ½, ¼, ⅛, ¹⁄₁₆, or ¹⁄₃₂ compared to a composition having 40 D antigen units for PV1, 8 D antigen units for PV2, and/or 30 D antigen units for PV3 (e.g., a normal 1× human dose).

In some embodiments, an immunogen and/or composition of the present invention (e.g., vaccine) may stimulate neutralization titers that are equal to or increased/greater than an accepted neutralization titer that correlates with protection from infection and/or disease for poliovirus (e.g., a titer of 8 and/or 3-$Log_2$) when the antigenic mass (e.g., D antigen content) of the poliovirus immunogen is in an amount that is less than (e.g., at least about 50%, 25%, 12.5%, or 6% less than) an antigenic mass (e.g., D antigen content) in a standard human dose for a current commercial poliovirus vaccine (e.g., an oral poliovirus vaccine and/or an inactivated poliovirus vaccine that is not inactivated using ionizing radiation (e.g., a formaldehyde and/or formalin inactivated poliovaccine)). In some embodiments an immunogen and/or composition of the present invention may have a D antigen content by mass (e.g., D antigen units per gram weight (e.g., per microgram or milligram)) that is equal to or increased/greater than the D antigen content by mass of a current commercial poliovirus vaccine (e.g., an oral poliovirus vaccine and/or an inactivated poliovirus vaccine that is not inactivated using ionizing radiation (e.g., a formaldehyde and/or formalin inactivated poliovaccine). For example, in some embodiments, a method of the present invention may be more gentle and/or may cause less damage to epitopes as compared to formalin inactivation. Thus, 1 mg of an immunogen of the present invention may have a higher D antigen content as compared to a formalin/formaldehyde-inactivated poliovirus and, therefore, may permit the production of a larger number of doses per unit of virus compared to formalin/formaldehyde-inactivated poliovirus. In some embodiments an immunogen and/or composition (e.g., a vaccine) of the present invention may have a D antigen content by mass (e.g., D antigen units per gram weight) that is increased by at least about 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500% or more as compared to a current commercial poliovirus vaccine (e.g., an oral poliovirus vaccine and/or an inactivated poliovirus vaccine that is not inactivated using ionizing radiation (e.g., a formaldehyde and/or formalin inactivated poliovaccine).

An immunogen and/or composition of the present invention may be provided and/or packaged in any suitable package and/or container. In some embodiments, an immunogen and/or composition of the present invention may be provided in a package suitable for administering the immunogen and/or composition to a subject. In some embodiments, glass vials, ampules, or other containers known to those of skill in the art may comprise an immunogen and/or composition of the present invention, optionally in single or multiple doses.

The amount of an immunogen administered to a subject and/or present in composition of the present invention is typically an amount sufficient to induce the desired immune response in the target host. Generally, the dosage employed may be about 0.1 microgram to about 100 micrograms of protein per dose (e.g., about 0.1, 0.2, 0.5, 1, 2, 3, 4, 5, 6, 7, 8, 9, 10, 15, 20, 25, 30, 35, 40, 45, 50, 55, 60, 65, 70, 75, 80, 85, 90, 95, or 100 micrograms of protein per dose, or any value or range therein). In some embodiments, the dosage may be calculated using the D antigen concentration. The dosage may or may not correlate with the D antigen content of currently licensed IPV vaccines which are composed of 40, 8, and 32 D antigen units of PV1, -2, and -3, respectively. In some embodiments, a composition (e.g., vaccine) of the present invention may comprise at least one antigen in an amount that is at least about 10% less than the amount in an IPV vaccine (e.g., at least about 10%, 15%, 20%, 25%, 30%, 35%, 40%, 45%, 50%, 55%, 60%, 65%, 70%, 75%, 80%, 85%, 90%, or 95% less than in an IPV vaccine (e.g., current commercial IPV vaccine, e.g., IPOL and/or VeroPol). For example, in some embodiments a composition of the present invention may comprise at least one PV1 antigen in an amount that is at least about 10% to about 55% less than in an IPV vaccine, may comprise at least one PV2 antigen in an amount that is at least about 20% to about 60% less, than in an IPV vaccine, or may comprise at least one PV3 antigen in an amount that is at least about 15% to about 50% less than in an IPV vaccine.

The irradiation-inactivated poliovirus immunogens of the present invention may be used to stimulate protective immunity in a subject (e.g., a human). The immunogens may be injected intramuscularly, intradermally, subcutaneously, and/or the like, into animals and/or humans, optionally using a standard syringe. In some embodiments, an immunogen of the present invention may be introduced into animals or humans using microneedles, patches designed to allow immunogens to penetrate the skin surface, and/or other methods known to the art.

In some embodiments, a manufacturing process for an immunogen of the present invention may include a procedure in which the immunogen is dried (e.g., desiccated by lyophilization, spray-drying, and/or the like). In some embodiments, the drying may increase the thermostability (e.g., by at least 10%, 15%, 20%, 25%, 30%, 35%, 40%, 45%, 50%, 55%, 60%, or more) of the immunogen and/or a composition comprising the immunogen and/or the drying may extend the shelf-life of the immunogen and/or a composition comprising the immunogen as measured (e.g., by at least 10%, 15%, 20%, 25%, 30%, 35%, 40%, 45%, 50%, 55%, 60%, or more), optionally by maintaining the immunogenic nature of the composition. The drying process may include compounding an immunogen of the present invention with one or more stabilizing excipient(s) known to those of skill in the art such as, but not limited to, sorbitol, trehalose, sucrose, polyethylene glycol, amino acids, and/or other additives. The drying procedure may utilize freeze-drying such as, e.g., lyophilization, spray-drying, and/or other methods known in the art.

In some embodiments, an adjuvant may be present in a vaccine of the present invention and the adjuvant may optionally stimulate an improved immune response. Example adjuvants include, but are not limited to, alum, aluminum hydroxide, aluminum phosphate, monophosphoryl Lipid A, saponin derivatives (e.g., QS-21), nucleic acids including oligonucleotides such as CpG, lipopolysaccharides, oil-and-water emulsions, squalene, saponin, and/or other adjuvanting substance(s) (e.g., flagellin).

The present invention is explained in greater detail in the following non-limiting examples.

EXAMPLES

Example 1: Poliovirus Serotype 2 Sabin Strain (PV2S)

The irradiation process included exposing virus preparations to radiation on wet ice. In the process, poliovirus was mixed with an antioxidant composition comprising 3 mM $MnCl_2$, 3 mM of the decapeptide DEHGTAVMLK (SEQ ID NO:1), and 50 mM phosphate buffer (pH 7.2), packaged into polypropylene tubes, purged of ambient air using argon, and exposed to either x- or gamma-irradiation. In the present example, the viruses were inactivated on ice using a radioactive Cobalt-60 source with appropriate shielding to protect the human user from harmful radiation.

Once compounded with the MDP complex, the virus was exposed to 0 to 50 kGy of gamma-irradiation. FIG. 1 shows the effects of gamma-irradiation in a dose-dependent manner on the viability of PV2-Sabin. In the left panel of FIG. 1, the virus infectivity is graphed in a semi-log plot against the dose of gamma-irradiation to a maximum of 35 kGy. In the inset of FIG. 1, the virus infectivity is graphed in a linear plot. The graphs show that 45 kGy of gamma-irradiation is sufficient to destroy 100% of the infectivity of a virus preparation including 16 micrograms of purified PV2S.

Figure 2:
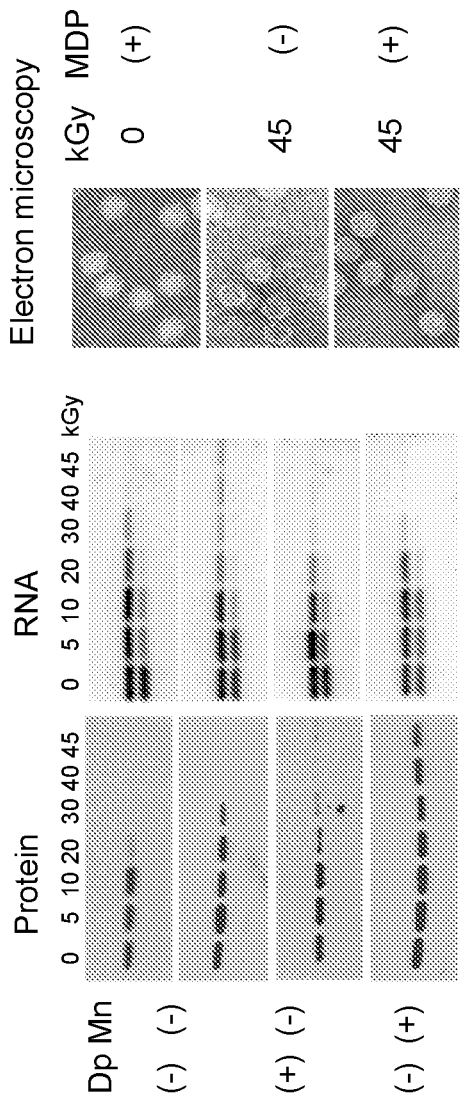

When compounded with the MDP complex, the surface capsid proteins of the virus are protected from degradation. FIGS. 2A-2C show three analyses of irradiated PV2. In the study, PV2-Sabin was exposed to 0, 5, 10, 20, 30, 40 and 45 kGy of irradiation. In FIGS. 2A and 2B, the virus was mixed with Decapeptide (Dp) and $MnCl_2$ ($Mn^{2+}$) (lower panels), or $Mn^{2+}$ only or Dp only (middle panels) or neither (upper panels) prior to irradiation. For FIG. 2A, samples of the irradiated virus were denatured with sodium dodecylsulfate (SDS) and 2-mercaptoethanol (2-ME), electrophoresed in a polyacrylamide gel, transferred to membranes, and probed with an antibody to the VP1 capsid protein. The figure shows that the inclusion of both Dp and $Mn^{2+}$ prior to irradiation leads to protection of the protein components (lower panel). For FIG. 2B, RNA was extracted from the irradiated virus samples and reverse transcribed using oligo(dT) to produce libraries of cDNA from the genomic poly(A) tract. The cDNA was used as a template in polymerase chain reactions (PCR) to assess the fragmentation of the genomic RNA with increasing irradiation. The PCR products were electrophoresed in a 2% agarose gel and the DNA fragments were visualized using ethidium bromide staining. The upper band was synthesized using primers corresponding to nucleotides 6786 to 7403 (617 base pairs located close to the site of cDNA priming) The lower band was synthesized using primers corresponding to nucleotides 5478-5941 (463 base pairs located further away from the site of cDNA priming) FIG. 2B demonstrates that the presence of the MDP complex during irradiation (lower panel) does not protect the RNA from damage. As anticipated, the signal from the lower band is reduced more rapidly than the signal from the upper band due to its increased distance from the site of cDNA synthesis priming in the poly(A) tract. Thus, FIGS. 2A and 2B show that the MDP complex allows protection of the viral proteins while not protecting the genome from fragmentation and inactivation. FIG. 2C shows transmission electron micrographs of non-irradiated (top) and irradiated virus (middle and lower). In the presence of MDP, the virus particles appear to be unfragmented compared to those irradiated without MDP.

Prior to analysis of the immunogenicity of the irradiated virus, the inactivated virus preparations were normalized for D antigen concentration for comparison to commercially-manufactured vaccines, IPOL® (Sanofi Pasteur) and VeroPol® (Staten Serum Institute, Denmark). The D antigen assay is a measure of antigenicity and has been used to predict the immunogenicity of vaccine preparations, wherein a higher D antigen content correlates with higher immunogenicity. The assay is performed in a solid-phase enzyme-linked antibody detection format and is highly standardized. The irradiated virus preparations were standardized to a 1× human dose which includes 40 D antigen units of PV1, 8 D antigen units of PV2, and 32 D antigen units of PV3.

Immunization of Wistar rats is a commonly used method for testing the immunogenicity of poliovirus vaccines. The animals are immunized by intramuscular injection of vaccine or test antigens and the rat sera sampled 35 and 49 days after the initial immunization is analyzed for virus neutralizing antibodies. A neutralization titer of 1:8 is accepted as a level of antiviral antibodies that conveys protection from infection and/or disease.

In a quantitative neutralization assay, serial 2-fold dilutions of antibody are incubated with 100 tissue culture infection units (TCID50) of virus for 1 hour. The antibody-virus complexes are applied to replicate well containing indicator cells that are tropic for poliovirus, such as MRC-5 cells, for 1 hour and then unbound material is washed off using a standard phosphate buffered saline (PBS) solution. Standard growth media is added to the wells and the plates are incubated at 37° C. for 3-4 days to allow for virus replication. The wells are scored as infected or non-infected microscopically. The neutralization titer is calculated using a Karber formula and expressed as the reciprocal of the dilution of serum that causes a 50% reduction in the number of infected wells.

Figure 3:
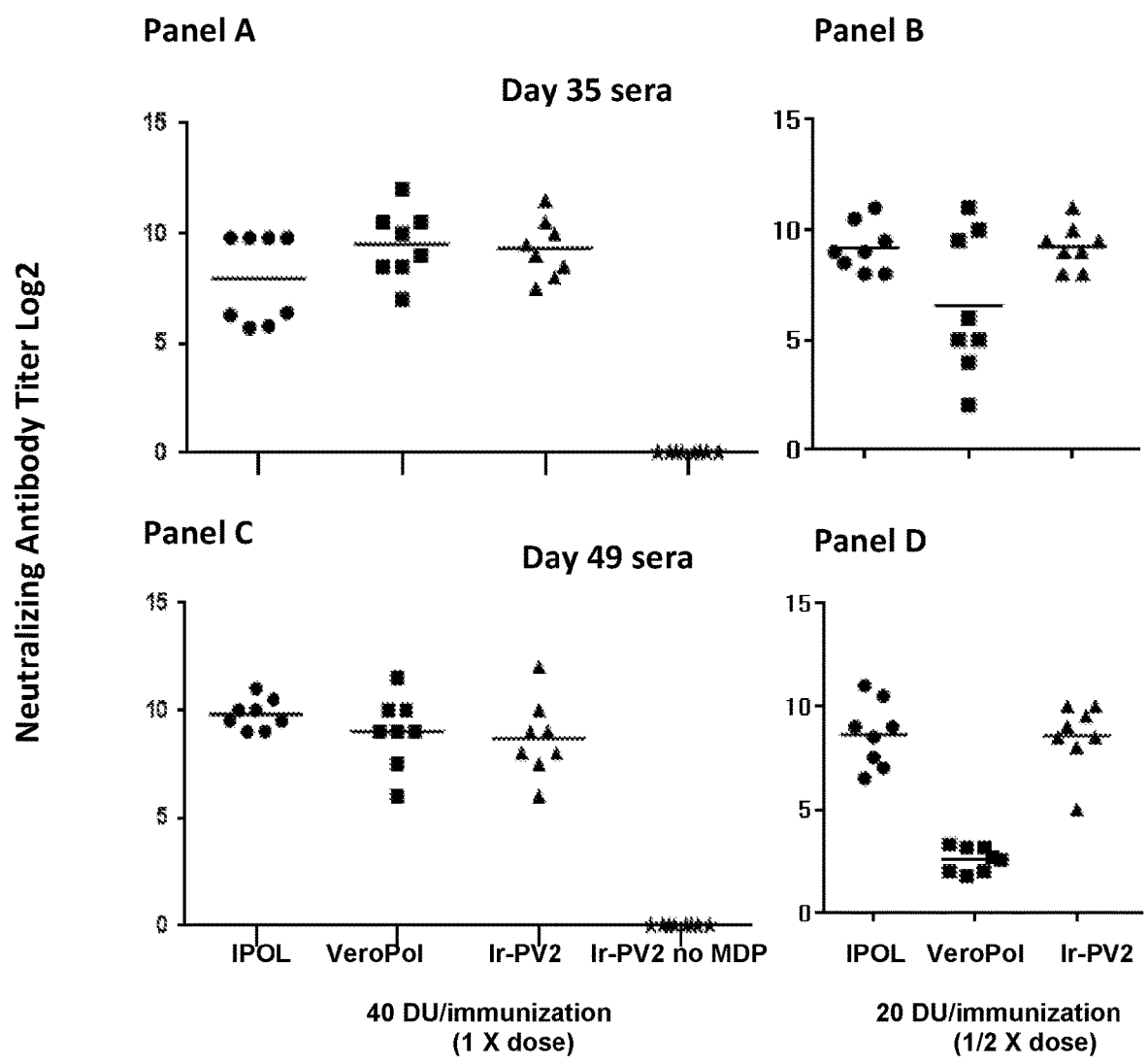
Figure 3:
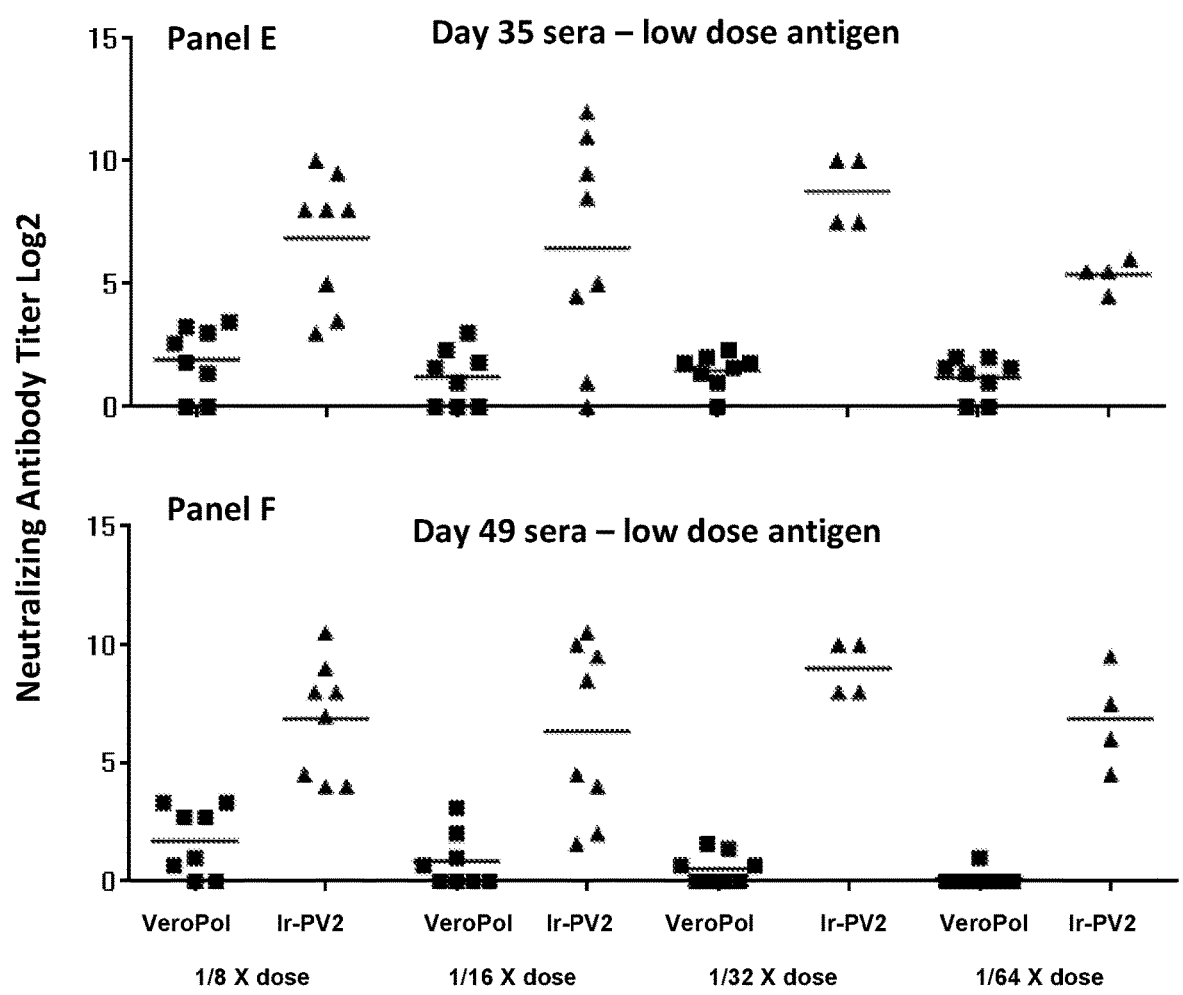

The immunogenicity of irradiation-inactivated type 2 Sabin strain (Ir-PV2S) was compared to IPOL and VeroPol in a Wistar rat immunization study Immunization with a 1× or 0.5× dose of Ir-PV2S stimulated roughly equivalent titers of anti-PV2 neutralizing antibodies as did IPOL (FIG. 3 panels A, B, C, and D).

The immunogenicity of Ir-PV2S and VeroPol were compared using decreasing doses of antigen. In addition to a comparison between the two antigens, the study was performed to determine whether reduced doses could stimulate protective levels of neutralizing antibodies for dose-sparing reasons. FIG. 3 panels E and F show the anti-PV2 neutralization titers for individual rat sera in the groups that were immunized with decreasing amounts of immunogen. In the left-most pair of data points, sera from rats immunized with a ⅛ (one eighth) dose of antigen (1 D antigen unit) demonstrate that the Ir-PV2S sera (shown as triangles) has higher neutralization titers compared to the anti-VeroPol sera. The figure shows that further reduction of the VeroPol dose stimulates little, if any, detectable PV2 neutralizing antibodies. In contrast amounts of Ir-PV2S as low as 1/64 (one sixty-fourth) of a normal human dose or 0.125 D antigen unit were sufficient to stimulate neutralizing antibodies.

Example 2: Poliovirus Serotype 1 Sabin Strain (PV1S)

PV1S was inactivated using gamma-irradiation. In the process, PV1S was mixed with an antioxidant composition comprising 3 mM $MnCl_2$, 3 mM of the decapeptide DEHGTAVMLK (SEQ ID NO:1), and 50 mM phosphate buffer (pH 7.2), and packaged into polypropylene tubes. The ambient air was purged with argon to remove dioxygen and the tubes were exposed to gamma-irradiation. In the present example, the viruses were inactivated on ice using a radioactive Cobalt-60 source (~12 kGy/hr) with appropriate shielding to protect the human user from harmful radiation.

Figure 4:
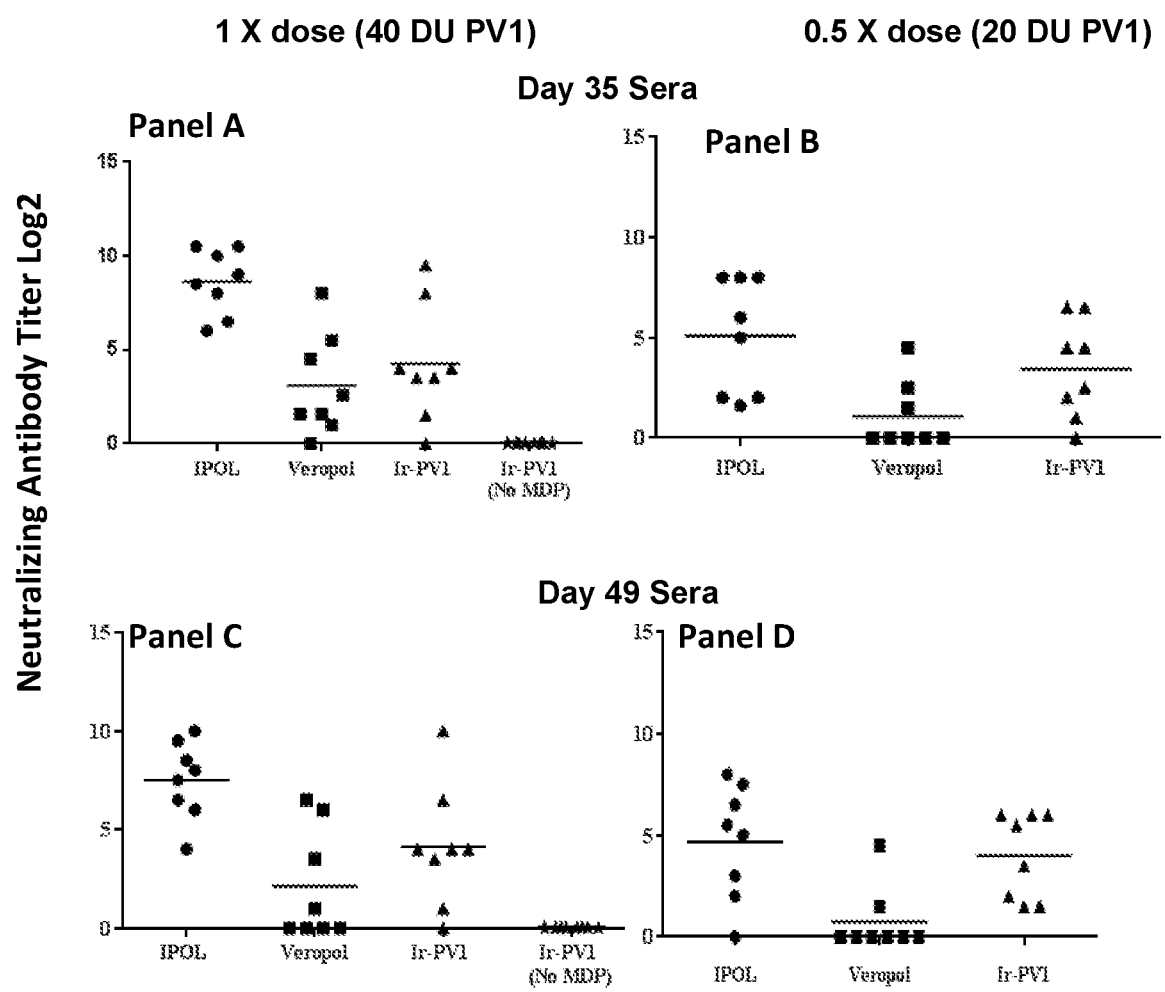

The immunogenicity of irradiation-inactivated poliovirus type 1 Sabin strain (Ir-PV1S) was compared to IPOL and VeroPol in the Wistar rat immunization model. Groups of 8 rats were immunized with either 1× or 0.5× human dose equivalent which contains 40 or 20 D antigen units of PV1 antigen, respectively. A control group of rats was immunized with virus that had been irradiated without the addition of the MDP complex. FIG. 4 shows the neutralization titers of serum samples from rats 35 and 49 days after the initial immunization with the four antigens. Serum from rats immunized with a 1× dose of IPOL are shown as circles, with 1× dose of VeroPol are shown as squares, with 1× dose of Ir-PV1S with MDP as triangles and with 1× dose of Ir-PV1 without MDP as circles. Sera from rats immunized with a half dose (0.5×) are shown in the right panels. The horizontal lines show the mean titers of the rat groups as expressed as Log-2 values. With the 1× dose or Ir-PV1S, 6 of the 8 rats seroconverted to the protective titer level of 8 or 3-$Log_2$. In contrast none of the rats immunized with Ir-PV1S produced in the absence of the MDP complex seroconverted. At the half-dose (0.5×), the Ir-PV1S stimulated roughly equivalent titers as IPOL administered at the same dose (right panels).

Example 3: Inactivation of PV1 Sabin with UVC Radiation

Poliovirus can be inactivated by exposure to UVC light without appreciable destruction of neutralizing epitopes. PV1 Sabin was complexed with MDP containing 3 mM DP1 decapeptide, 3 mM $MnCl_2$ and 50 mM potassium phosphate buffer, pH 7.2. The virus-MDP complex was placed into tubes that are transparent to UVC light. The samples were exposed for 60 minutes to a UVC light that emits 0.7 $mW/cm^2$ or for 2 minutes to a UVC light that emits 5 $mW/cm^2$. The inactivation process was assessed with the use of standard infectivity assays. The irradiation inactivates the infectivity of poliovirus more rapidly when the virus is placed into thin-walled UVC-transparent tubes. In follow-up studies, irradiation for as little as 10 or 20 seconds with a light that emits 5 $mW/cm^2$ inactivated all detectable infectivity (data not shown).

The immunogenicity of the UVC-inactivated poliovirus can be assessed by the analysis of sera from immunized rats. Wistar rats were immunized by intramuscular injection with 40 D antigen units, a 1× human dose, of UVC-inactivated PV1 Sabin on Days 0 and 21. No adjuvant was used. Four weeks later, on Day 49, serum samples were collected from the rats for the analysis of neutralizing antibodies. FIG. 5 shows linear titers and Log-2 titers of neutralizing activities from sera generated from rats immunized with UVC-inactivated PV1. The mean Log 2 titer of the sera from PV1 Sabin with MDP was 9.7 which correlates to a linear titer of 1,960. The mean Log 2 titer of the sera from PV1 Sabin without MDP was 4.4 which correlates to a titer of 1:229.3. The data from FIG. 5 is graphed in FIG. 6. FIG. 6 shows graphs of the Log-2 titers of the sera from rats immunized with UVC-irradiated PV1 Sabin with MDP (closed circles) and without MDP (open circles). Horizontal lines indicate mean Log-2 titers.

Example 4: Inactivation of PV3 Sabin with UVC Light

Not all viruses can be inactivated with gamma irradiation without damage to protective epitopes. In the case of PV3 Sabin, exposure to 40 kGy of gamma irradiation resulted in antigens that appeared to be intact by Western blot analysis but had greatly reduced D antigen concentrations. In multiple experiments, the amount of D antigen was reduced from approximately 60,000 units per mL to undetectable levels (data not shown). As anticipated, rats immunized with PV3 Sabin-MDP complexes that were inactivated of infectivity with gamma irradiation did not mount acceptable anti-PV3 neutralizing titers (data not shown).

Figure 7:
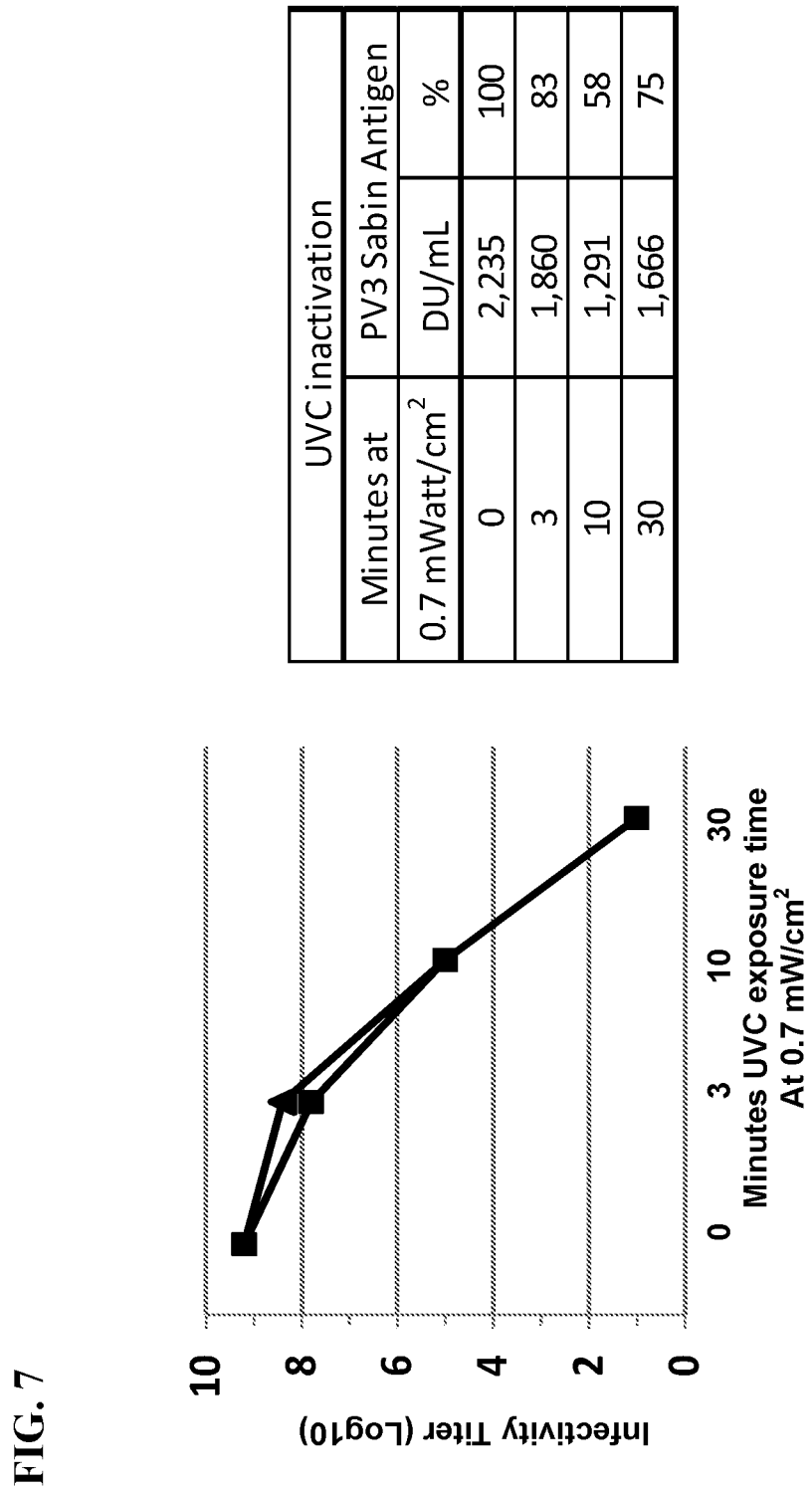

Inactivation of PV3 Sabin by exposure to UVC light was investigated. As with PV1 Sabin, samples of virus were complexed with or without MDP (3 mM Dp1 decapeptide, 3 mM $MnCl_2$, and 50 mM potassium phosphate buffer, pH 7.2). After exposure to a UVC light that emits 0.7 $mW/cm^2$ for 3, 10, and 30 minutes, the samples were titered for infectivity using Hela cells. The left panel of FIG. 7 shows the Log-10 infectivity titers of the PV3 Sabin exposed to UVC with (circles) or without (triangles) MDP. The infectivity titer curves show little differences indicating that the presence or absence of the MDP complex provides little, if any, effect on inactivation of infectivity. PV3 Sabin samples treated with UVC light in the presence of the MDP complex were assessed for protection of viral epitopes that stimulate neutralizing antibodies using a D antigen ELISA assay (FIG. 7, right panel). The high-dose of UVC irradiation inactivates almost all infectivity yet reduces the D antigen concentration by only 25%. An exposure of 60 minutes from the same UVC source inactivates 100% infectivity while maintaining immunogenic activity of the neutralizing epitopes.

Rats were immunized with UVC-inactivated PV3 Sabin to provide a more definitive measure of immunogenicity. In this experiment, PV3 Sabin samples with and without MDP were exposed for 60 minutes to a UVC light emitting 0.7 mW/cm² and found to lack detectable infectivity. Duplicate samples were analyzed for D antigen concentration and reduced antigen doses. At a dose equivalent to ⅛ of a standard human dose, UVC-inactivated PV3 Sabin stimulated neutralizing titers above the accepted protective titer of 3-Log 2 when irradiated in the presence of the MDP complex.

The foregoing is illustrative of the present invention, and is not to be construed as limiting thereof. The invention is defined by the following claims, with equivalents of the claims to be included therein. All publications, patent applications, patents, patent publications, and other references cited herein are incorporated by reference in their entireties for the teachings relevant to the sentence and/or paragraph in which the reference is presented.

```
                        SEQUENCE LISTING

<160> NUMBER OF SEQ ID NOS: 3

<210> SEQ ID NO 1
<211> LENGTH: 10
<212> TYPE: PRT
<213> ORGANISM: artificial
<220> FEATURE:
<223> OTHER INFORMATION: peptide

<400> SEQUENCE: 1

Asp Glu His Gly Thr Ala Val Met Leu Lys
1               5                   10

<210> SEQ ID NO 2
<211> LENGTH: 4
<212> TYPE: PRT
<213> ORGANISM: artificial
<220> FEATURE:
<223> OTHER INFORMATION: peptide

<400> SEQUENCE: 2

His Met Leu Lys
1

<210> SEQ ID NO 3
<211> LENGTH: 6
<212> TYPE: PRT
<213> ORGANISM: artificial
<220> FEATURE:
<223> OTHER INFORMATION: peptide

<400> SEQUENCE: 3

His Met His Met His Met
1               5
``` samples corresponding to a 2×, 1×, ½×, and ⅛× human dose (64, 32, 16, and 4 D antigen units, respectively) were formulated without adjuvant. Rats were immunized by intramuscular injection on Days 0 and 21 and bled for sera on Day 49. FIG. 8 shows the linear and Log-2 titers of neutralizing activities from sera generated from rats immunized with UVC-inactivated PV3 Sabin Mean values for each group are also shown. FIG. 9 graphs the data shown in FIG. 8. FIG. 9 shows the Log-2 titers for individual rats immunized with PV3 Sabin with MDP (closed symbols) or without MDP (open symbols). The horizontal lines indicate the mean group titers. The inclusion of MDP improves the protection of the neutralizing epitopes during UVC-inactivation. The effect of MDP on improving the neutralization titers is more prominent when rats are immunized with That which is claimed is:

1. A method of producing an inactivated poliovirus immunogen, the method comprising:
    exposing a poliovirus to a divalent cation which is $Mn^{2+}$, a peptide which comprises any one or any combination of SEQ ID NO:1-3, and a phosphate buffer; and then
    exposing the poliovirus in the presence of the divalent cation, peptide, and buffer to ultraviolet radiation in an amount sufficient to inactivate the poliovirus, thereby providing the inactivated poliovirus immunogen, wherein the poliovirus immunogen stimulates neutralizing antibodies as determined in the standard Wistar rat model when administered to a subject.

2. The method of claim 1, wherein the poliovirus comprises an attenuated strain of poliovirus serotype 1, 2, and/or 3.

3. The method of claim 1, wherein the composition comprises the divalent cation in a concentration of about 1 mM to about 10 mM, the peptide in a concentration of about 0.5 mM to about 10 mM, and a phosphate buffer in a concentration of about 10 mM to about 100 mM.

4. The method of claim 1, wherein the method comprises exposing the poliovirus to ionizing radiation and then exposing the poliovirus to ultraviolet radiation.

5. The method of claim 1, further comprising, prior to exposing the poliovirus to ultraviolet radiation, at least partially replacing air in contact with the poliovirus and/or in a container comprising the poliovirus with a non-reactive gas.

6. The method of claim 1, wherein at least a portion of the epitopes of the poliovirus are undamaged and/or active in the inactivated poliovirus immunogen.

7. The method of claim 1, wherein the buffer comprises a potassium phosphate buffer.

8. The method of claim 1, wherein the peptide is HMLK (SEQ ID NO:2), HMHMHM (SEQ ID NO:3), or DEHGTAVMLK (SEQ ID NO:1).

9. The method of claim 1, wherein the divalent cation is provided by manganese chloride.

10. The method of claim 1, wherein the poliovirus comprises one or more attenuated Sabin strain(s).

11. The method of claim 10, wherein the poliovirus comprises one or more S19 strain(s).

12. The method of claim 1, wherein the poliovirus immunogen stimulates neutralizing antibodies in an amount substantially similar to or greater than the amount of neutralizing antibodies provided by a poliovirus immunogen inactivated using UV radiation in the absence of an antioxidant composition and/or than a poliovirus immunogen inactivated using formaldehyde and/or formalin.

13. The method of claim 1, wherein the poliovirus immunogen stimulates neutralization titers in an amount equal to or greater than a titer of 8 at a dose comprising irradiation inactivated PV1 serotype having a D antigen content of less than 40 D antigen units, an irradiation inactivated PV2 serotype having a D antigen content of less than 8 D antigen units, and/or an irradiation inactivated PV3 serotype having a D antigen content of less than 32 D antigen units.

14. The method of claim 1, wherein the method produces the inactivated poliovirus immunogen with a greater D antigen content by mass than a formaldehyde and/or formalin inactivated poliovirus vaccine and/or an inactivated poliovirus vaccine that is not inactivated using ionizing radiation.

15. The method of claim 1, wherein the method produces of a larger number of doses per unit of the poliovirus compared to a method of preparing a current commercial polio vaccine, optionally wherein the method of preparing the current commercial polio vaccine uses formaldehyde and/or formalin.

16. The method of claim 1, further comprising drying the inactivated poliovirus immunogen.

17. A method of producing an inactivated poliovirus immunogen, the method comprising:
   exposing a poliovirus to a divalent cation which is $Mn^{2+}$, a peptide which comprises any one or any combination of SEQ ID NO:1-3, and a phosphate buffer;
   at least partially replacing air in contact with the poliovirus and/or in a container comprising the poliovirus with a non-reactive gas; and then
   exposing the poliovirus to ionizing radiation and/or ultraviolet radiation in an amount sufficient to inactivate the poliovirus, thereby providing the inactivated poliovirus immunogen.

* * * * *

UNITED STATES PATENT AND TRADEMARK OFFICE
CERTIFICATE OF CORRECTION

PATENT NO. : 12,042,533 B2
APPLICATION NO. : 17/041870
DATED : July 23, 2024
INVENTOR(S) : Tobin et al.

It is certified that error appears in the above-identified patent and that said Letters Patent is hereby corrected as shown below:

In the Specification

Column 4, Line 25: Please correct "MRCS" to read --MRC5--

Column 5, Line 55: Please correct "5%" to read --±5%--

Column 9, Line 36: Please correct "MRCS" to read --MRC5--

Column 11, Line 15: Please correct "(I Omer)" to read --(10mer)--

Column 20, Line 6: Please correct "($Mn^{2'}$)" to read --($Mn^{2+}$)--

Signed and Sealed this
Fifth Day of November, 2024

Katherine Kelly Vidal
*Director of the United States Patent and Trademark Office*